(12) United States Patent
Muraca

(10) Patent No.: US 8,278,034 A0
(45) Date of Patent: Oct. 2, 2012

(54) METHODS OF MAKING FROZEN TISSUE MICROARRAYS

(75) Inventor: Patrick J. Muraca, Pittsfield, MA (US)

(73) Assignee: Nuclea Biotechnologies, Inc., Pittsfield, MA (US)

( * ) Notice: Subject to any disclaimer, the term of this patent is extended or adjusted under 35 U.S.C. 154(b) by 0 days.

(21) Appl. No.: 09/888,362

(22) Filed: Jun. 22, 2001

(65) Prior Publication Data

US 2002/0009767 A1    Jan. 24, 2002

Related U.S. Application Data

(60) Provisional application No. 60/213,321, filed on Jun. 22, 2000, provisional application No. 60/234,493, filed on Sep. 22, 2000, provisional application No. 60/236,649, filed on Sep. 29, 2000.

(51) Int. Cl.
*C12Q 1/68* (2006.01)
*C12N 11/16* (2006.01)
*G01N 15/06* (2006.01)

(52) U.S. Cl. ............ 435/6; 435/7.1; 435/40.5; 435/174; 435/283.1; 435/287.2; 536/23.1; 422/68.1

(58) Field of Classification Search ............... 435/286.3, 435/284.1, 286.2, 307.1, 307.9, 6, 91.1, 174, 435/283.1, 287.2, 40.5, 7.1; 536/23.1; 422/68.1
See application file for complete search history.

(56) References Cited

U.S. PATENT DOCUMENTS

| | | | | |
|---|---|---|---|---|
| 4,647,548 A | | 3/1987 | Klein | 501/134 |
| 4,914,022 A | | 4/1990 | Furmanski et al. | 435/7 |
| 5,002,377 A | * | 3/1991 | Battifora et al. | 359/398 |
| 5,533,342 A | * | 7/1996 | Gordon | 62/51.1 |
| 5,804,384 A | | 9/1998 | Muller et al. | 435/6 |
| 5,843,684 A | | 12/1998 | Levine et al. | 435/7.23 |
| 5,998,136 A | | 12/1999 | Kamb | 435/6 |
| 6,010,846 A | | 1/2000 | Hellerstein | 435/4 |
| 6,046,307 A | | 4/2000 | Shay et al. | 530/324 |
| 6,103,479 A | | 8/2000 | Taylor | 435/7.2 |
| 6,103,518 A | * | 8/2000 | Leighton | 435/286.3 |
| 6,136,592 A | | 10/2000 | Leighton | 435/288.7 |
| 6,165,709 A | | 12/2000 | Friend et al. | 435/4 |
| 6,406,840 B1 | * | 6/2002 | Li et al. | 435/1.3 |
| 6,534,307 B1 | | 3/2003 | Muraca | 435/286.2 |
| 6,582,967 B2 | * | 6/2003 | Muraca | 436/174 |

(Continued)

FOREIGN PATENT DOCUMENTS

EP    0 238 190    2/1987

(Continued)

OTHER PUBLICATIONS

Irving et al. (J of Clin. Path. (1996) 49: 258-259).*

(Continued)

*Primary Examiner* — B J Forman

(74) *Attorney, Agent, or Firm* — Paula C. Evans

(57) ABSTRACT

The invention provides microarrays comprising a plurality of frozen tissues and/or cell samples and methods of preparing and using the same. By using frozen samples, the microarrays provide optimal samples from which to detect the expression of both nucleic acids (e.g., mRNAs) and proteins in high throughput parallel analyses. The microarrays enable gene identification, molecular profiling, selection of promising drug targets, sorting and prioritizing of expressed sequence array data, and the identification of abnormal physiological processes associated with disease.

13 Claims, 4 Drawing Sheets

U.S. PATENT DOCUMENTS 6,699,710 B1 * 3/2004 Kononen et al. ............ 435/283.1
2002/0132246 A1 * 9/2002 Kallioniemi et al. ............. 435/6

FOREIGN PATENT DOCUMENTS

| EP | 1 026 260 | 8/2000 |
| WO | 99/43855 | 9/1999 |
| WO | 99/44062 | 9/1999 |
| WO | 99/44063 | 9/1999 |

OTHER PUBLICATIONS

Goldsworthy et al. (Mol. Carcinog (1999) 25(2): 86-91).*
Moch, et al., "Tissue Microarrays: What Will They Bring to Molecular and Anatomic Pathology," Advances in Anatomic Pathology 8(1): Jan. 14-20, 2001.

* cited by examiner

METHODS OF MAKING FROZEN TISSUE MICROARRAYS

RELATED APPLICATIONS

This application claims priority under 35 U.S.C. § 119(e) to U.S. Provisional Application Ser. No. 60/213,321, filed Jun. 22, 2000, U.S. Provisional Application No. 60/234,493, filed Sep. 22, 2000, and U.S. Provisional Application No. 60/236,649, filed Sep. 29, 2000, the entireties of which are incorporated by reference herein.

FIELD OF THE INVENTION

The present invention relates to frozen tissue arrays and methods of arraying frozen tissue samples for high throughput molecular analyses.

BACKGROUND OF THE INVENTION

The microscopic examination and classification of tissues has improved medical treatment. For example, in the case of many tumors, a diagnosis can be made on the basis of cell morphology and staining characteristics. Even the aggressiveness of a tumor can sometimes be predicted through microscopic evaluation. However, standard staining methods such as hematoxylin-eosin (H&E) generally can reveal only a limited amount of diagnostic information.

Recent advances in molecular medicine have provided the opportunity to understand the cellular mechanisms of disease and to select appropriate treatments. The identification of molecular markers of disease, such as tumor-specific antigens, enables diagnostic and prognostic assays to be developed which rely on the use of molecular probes (e.g., antibodies and nucleic acid probes) to detect these markers. However, the development of new molecular markers of clinical importance has been impeded by the slow and tedious process of determining the expression of these markers in large numbers of clinical specimens. For example, hundreds of tissue specimens representing different stages of tumor progression must be evaluated before the biological relevance of a given marker can be confirmed. As the number of molecular probes increases, the number of tissue samples which can be evaluated in a single experiment becomes a rate-limiting factor.

Prior to 1998, methods of grouping multiple tissue specimens on a single substrate relied on manually cutting multiple paraffin-embedded tissue specimens and forming them into a composite block (see, e.g., Battifora et al., 1986, *Lab. Invest.* 55: 244–248; U.S. Pat. No. 4,820,504) or into "straws" or "logs" from which transverse sections could be obtained (see, e.g., Wan et al., 1987, *J. Immunol. Meth.* 103: 121–129; U.S. Pat. No. 4,914,022; Miller and Groothuis, 1991, *A.J.C.P.* 96: 228–232). In addition to requiring a high degree of manual dexterity, these methods randomly arranged samples, making it difficult to identify specimens of interest. Methods to overcome the problems of random placement by placing tissue strips in grooves within a mold have been described by Battifora and Mehta, 1990, *Lab. Invest.* 63: 722–724, U.S. Pat. No. 5,002,377 and Sunblad, 1993, A.J.C.P. 102: 192–193, however, these methods are also labor intensive and time consuming.

Kononen et al., 1998, *Nat. Med.* 4: 844–7, have recently described a technique for generating tissue arrays comprising hundreds of tumor specimens using punched samples from archival tissue blocks. While greatly increasing the throughput of methods involving the use of tissue microarrays, the technique has been limited to the evaluation of paraffin-embedded tissue specimens which are not optimal for many types of molecular analyses.

SUMMARY OF THE INVENTION

The invention provides microarrays comprising a plurality of frozen tissues and/or cell samples and methods of preparing and using the same. By using frozen samples, the microarrays provide optimal samples from which to detect the expression of both nucleic acids (e.g., mRNAs) and proteins in high throughput parallel analyses.

In one aspect, the invention provides a method for preparing a microarray of frozen tissue and/or cell samples comprising the steps of: providing a microarray block comprising a plurality of donor samples embedded in a block of frozen embedding material, each of the donor samples having a known location in the block, sectioning the block to generate a section comprising portions of the plurality of donor samples, each portion of each donor sample at a different sublocation in the section at coordinates corresponding to coordinates of the donor sample in the microarray block from which each portion was obtained. The section is then placed on a substrate such that the portions at different sublocations are stably associated with the substrate. The microarray block can comprise up to about 1200 samples, and preferably, comprises at least about 10–1200 samples.

The invention also provides a method for generating a microarray block. In one aspect, a microarray block is generated by obtaining a donor sample from a donor block comprising a tissue or cell sample embedded in frozen embedding material, providing a recipient block comprising a frozen embedding material and generating a hole in the recipient block sized to receive the donor sample, and filling the hole with the donor sample. Preferably, these steps are repeated multiple times until the recipient block is filled with a desired number of donor samples, thereby generating the microarray block. In one aspect, the steps are performed using an automated or semi-automated microarrayer device. Preferably, information relating to the location of each donor sample in the microarray block is stored in a database.

In one aspect, the donor sample is obtaining using a coring needle comprising a cutting edge and wall defining a lumen. The core generated by the cutting action of the coring needle can be any shape, but in one aspect, is in the shape of a cylinder. The core can also be a variety of sizes, for example, about 0.3 mm in diameter, about 0.6 mm in diameter, or greater than about 0.6 mm.

A variety of different types of tissue and/or cell samples can be placed in the block. In one aspect, at least one sample in the block is from a human. In another aspect, at least one sample is from an individual having a disease. In a further aspect, the disease is a progressive disease and the block comprises a plurality of samples representing different stages in the progression of the disease. In one aspect, the disease is cancer. In another aspect, the disease is a respiratory disease, an infectious disease, an immune disease, a disease affecting reproductive organs (male or female), a cardiovascular disease, a disease affecting the endocrine system, a disease affecting the urinary system, a disease affecting the digestive system, a neurodegenerative disease and/or a neuropsychiatric disease. In the case of a chronic disease, the microarray can comprise samples representing both remission periods and exacerbation periods.

In a preferred aspect, the microarray block comprises a plurality of different types of tissue samples from the same individual. Preferably, the block comprises at least about 5 or at least about 10 different types of tissues. More preferably, the block further comprises a cell sample (e.g., such as from a bodily fluid) from the individual.

In one aspect, at least one sample in the block is from a fetus.

In another aspect, at least one sample in the block is from a non-human animal. Preferably, the non-human animal is a model for a disease. In another aspect, the non-human animal comprises at least one cell comprising an exogenous nucleic acid. In a further aspect, the non-human animal has been treated with a therapy for treating the disease.

In still another aspect, the microarray block comprises at least one donor sample from a plant.

The invention further provides microarrays generated from any of the microarray blocks described above.

The invention also provides a method for evaluating a tissue or cell sample, comprising: providing any of the microarrays described above, contacting the microarray with a molecular probe and determining which sublocations of the microarray react with the molecular probe. In one aspect, evaluating comprises correlating reactivity of the probe with one or more characteristics of the individual from which a sample at a reacted sublocated was obtained. In another aspect, the one or more characteristics comprises the presence of a disease, such as cancer. Samples also can be provided from an individual treated with a drug for treating the disease.

The invention also provides a method for identifying or confirming the specificity of a molecular probe. The method comprises providing a microarray comprising a plurality of different frozen tissue samples from the same individual, reacting the microarray with a molecular probe, and determining which of the tissue samples react with the molecular probe. Preferably, the microarray comprises at least about five or at least about ten different tissue types. More preferably, the microarray comprises at least one cell sample from a bodily fluid from said individual.

The invention further provides a method for identifying a candidate diagnostic probe. The method comprises the steps of providing a molecular probe corresponding to a differentially expressed sequence, reacting the molecular probe with a plurality of microarrays comprising samples from individuals having a trait and from individuals not having the trait, and determining the presence or absence of a correlation between the reactivity of the probe and the trait, wherein the presence of a correlation identifies the probe as a diagnostic probe. In one aspect, the differentially expressed sequence is identified by performing electronic subtraction of an expressed sequence database. In another aspect, the differentially expressed sequence is identified by evaluating one or more of a nucleic acid array, a peptide array, a polypeptide array, or an array of cells from a plurality of cell culture lines.

The foregoing and other objects, features and advantages of the invention will become more apparent from the following detailed description of particular aspects.

BRIEF DESCRIPTION OF THE DRAWINGS

The objects and features of the invention can be better understood with reference to the following detailed description and accompanying drawings.

FIG. 3A shows a perspective view.

DETAILED DESCRIPTION OF THE PRESENT INVENTION

Figure 1A:
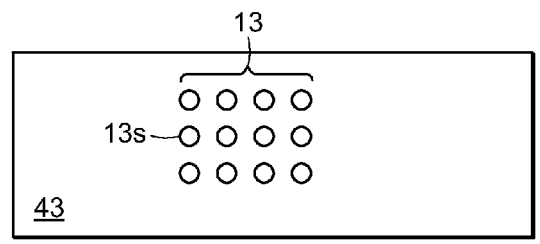
FIG. 1A is a schematic of a frozen microarray according to one aspect of the invention.

The invention provides a plurality of frozen tissue samples embedded in a single microarray block for generating hundreds of substantially identical frozen tissue microarrays and a precision instrument for generating the same. Frozen tissue microarrays according to the invention can be evaluated in high throughput parallel analyses using the same or different molecular probes, enabling gene identification, molecular profiling, selection of promising drug targets, sorting and prioritizing of expressed sequence array data, and the identification of abnormal physiological processes associated with disease.

Definitions

The following definitions are provided for specific terms which are used in the following written description.

The term "frozen" as used herein, refers to temperatures which are at least −20° C. or colder.

As used herein "donor block" refers to a fast-freezing embedding material comprising a frozen tissue or cell(s). While referred to as a "block", the embedded frozen tissue or cell(s) can be generally of any shape or size so long as an at least about 0.3 mm in diameter sample core can be obtained from it. A sample from a donor block can be placed directly onto a slide or can be placed in a recipient block.

As used herein "donor sample" refers to an embedded tissue or cell sample obtained from the donor block.

As used herein "recipient block" refers to a block formed from a fast-freezing embedding material which is capable of holding frozen donor samples in a pattern so that the location of the frozen donor samples relative to each other is maintained when the frozen block is sectioned to produce an array of frozen tissue and/or cell samples. The term "microarray block" refers more specifically to a recipient block which comprises a desired number of frozen donor samples.

As used herein a "tissue" is an aggregate of cells that perform a particular function in an organism and generally refers to cells and cellular material (e.g., such as extracellular matrix material) from a particular physiological region. The cells in a particular tissue can comprise several different cell types. A non-limiting example of this would be brain tissue that further comprises neurons and glial cells, as well as capillary endothelial cells and blood cells.

As used herein a "nucleic acid microarray," a "peptide microarray," a "polypeptide microarray," a "protein microarray," or a "small molecule microarray" or "arrays" of any of nucleic acids, peptides, polypeptides, proteins, small molecules, refer to a plurality of nucleic acids, peptides, polypeptides, proteins, or small molecules, respectively that are immobilized on a substrate in assigned locations (i.e., known locations).

As used herein "a tissue microarray" is a microarray that comprises a plurality of sublocations, each sublocation comprising tissue cells and/or extracellular materials from tissues, or cells typically infiltrating tissues, where the morphological features of the cells or extracellular materials at each sublocation are visible through microscopic examination. The term "microarray" implies no upper limit on the size of the tissue sample on the microarray, but merely encompasses a plurality of tissue samples which, in one aspect, can be viewed using a microscope.

As used herein a "large format microarray" comprises at least one sublocation comprising at least two different cell types (e.g., abnormally growing cells and normally growing cells, such as cancer cells and non-cancer cells), at least one cell type and extracellular matrix material, or a plurality of cells comprising at least one cell expressing a heterogeneously expressed biological characteristic (e.g., a biological characteristic expressed in less than 80% of cells of a given tissue or cell type). In one aspect, a large format tissue microarray comprises at least one sublocation being larger than 0.6 mm in at least one dimension. In contrast, a "small format" microarray comprises samples of about 0.6 mm in diameter and an "ultrasmall format" microarray comprises tissue samples less than about 0.6 mm in diameter (e.g., preferably, about 0.3 mm in diameter). "Mixed format" arrays comprise samples of varying sizes and include two or more of small format samples, large format samples, and ultrasmall format samples (see, e.g., FIG. 1C).

As used herein a "microarray sample" or "sample" refers to either a tissue sample or cell sample, unless specifically used in connection with the terms "nucleic acid microarray", "polypeptide array", "peptide array" or "small molecule" array.

As used herein "a portion of a donor sample" is a section through a donor sample.

As used herein, a portion of a sample which is "stably" associated with a substrate refers to a portion which does not substantially move from its position on the substrate during one or more molecular procedures.

As used herein "a cell sample" is distinguished from a tissue sample in that it comprises a cell or cell which is disassociated from other cells.

As used herein "a hole sized to receive a donor" sample refers to a hole in the recipient block which fits a donor sample snugly, so that there is no appreciable space between the donor sample and the walls of the hole (e.g., less than about 1 mm between the edge of a donor sample and the walls of the hole in the recipient block).

As used herein "different types of tissues" refers to tissues which are preferably from different organs or which are at least from anatomically and histologically distinct sites in the same organ.

As used herein "information relating to the location of each donor sample" is information which includes at least the coordinates of the donor sample in the block.

As used herein "substantially identical microarrays" refer to microarrays obtained by sectioning a single microarray block. Preferably, substantially identical microarrays comprise sections which are within about 0–500 µm of each other in a microarray block. Substantially identical microarrays comprise a one-to-one correspondence of samples, such that samples at identical coordinates in each of a plurality of microarrays will be substantially identical.

As used herein "coordinates" refer to the x, y location of a sample in a microarray comprising samples arranged in rows and columns, wherein the x coordinate refers to the column number of the sample and the y coordinate refers to the row number of the sample.

As used herein "substantially intact morphological features" refers to features which at least can be viewed under a microscope to distinguish subcellular features (e.g., such as a nucleus, an intact cell membrane, organelles, and/or other cytological features).

As used herein "molecular procedure" refers to contact with a test reagent or molecular probe such as an antibody, nucleic acid probe, enzyme, chromagen, label, and the like. In one aspect, a molecular procedure comprises one or more of a plurality of hybridizations, incubations, fixation steps, changes of temperature (from about −4° C. to about 100° C.), exposures to solvents, and/or wash steps.

As used herein "similar demographic characteristics" or "demographically matched", refers to patients who minimally share the same sex and belong to the same age grouping (e.g., are within about 5 to fifteen years of a selected age). Additional shared characteristics can be selected, including, but not limited to, shared place of residence (e.g., within a hundred mile radius of a particular location), shared occupation, shared history of illnesses, shared ethnic background, and the like.

As used herein a "molecular probe" is any detectable molecule or molecule which produces a detectable molecule upon reacting with a biological molecule. "Reacting" encompasses binding, labeling, or initiating an enzymatic reaction.

As used herein a "biological molecule" is any molecule which is found in a cell or within the body of an organism.

As used herein a "detectable binding reagent" refers to an agent that specifically recognizes and interacts or binds with an entity one wishes to measure, wherein the agent has a property permitting detection when bound. "Specifically interact" means that a binding agent physically interacts with the entity one wishes to measure, to the substantial exclusion of other entities also present in the sample. The binding of a detectable binding reagent useful according to the invention has stability permitting the measurement of the binding. A detectable binding reagent can possess an intrinsic property that permits direct detection, or it can be labeled with a detectable moiety.

As used herein "detectable moiety" refers to a moiety that can be attached to a binding reagent that confers detection of the binding reagent by a particular method or methods. Detectable moieties include, but are not limited to radiolabels (e.g., $^{32}P$, $^{35}S$, $^{125}I$, etc.), enzymes (e.g., alkaline phosphatase, peroxidase, etc.), fluorophores (e.g., fluorescein, amino coumarin acetic acid, tetramethylrhodamine isothiocyanate (TRITC), Texas Red, Cy3.0, Cy5.0, green fluorescent protein, etc.) and colloidal metal particles.

As used herein "antibody or antigen binding fragment thereof" refers to an immunoglobulin having the capacity to specifically bind a given antigen. The term "antibody" as used herein is intended to include whole antibodies of any isotype (IgG, IgA, IgM, IgE, etc), and fragments thereof which are also specifically reactive with a vertebrate, e.g., mammalian, protein. Antibodies can be fragmented using conventional techniques and the fragments screened for utility in the same manner as whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, $F(ab)_2$, Fab, Fv, and single chain antibodies (scFv) containing a $V_L$ and/or $V_H$ domain joined by a peptide linker. The scFv's can be covalently or non-covalently linked to form antibodies having two or more binding sites. Antibodies can be labeled with any detectable moieties known to one skilled in the art. In some aspects, the antibody that binds to an entity one wishes to measure (the primary antibody) is not labeled, but is instead detected by binding of a labeled secondary antibody that specifically binds to the primary antibody.

As used herein "difference in expression characteristics" or a gene which is "differentially expressed" refers to an increase or decrease in a measurable expression characteristic of a given polypeptide. A difference can be an increase or a decrease in a quantitative measure (e.g., amount of protein or RNA encoding the protein) or a change in a qualitative measure (e.g., location of the protein). Where a difference is observed in a quantitative measure, the difference according to the invention will be at least 10% greater or less than the level in a normal standard sample. Where a difference is an increase, the increase can be as much as 20%, 30%, 50%, 70%, 90%, 100% (2-fold) or more, up to and including 5-fold, 10-fold, 20-fold, 50-fold or more. Where a difference is a decrease, the decrease can be as much as 20%, 30%, 50%, 70%, 90%, 95%, 98%, 99% or even up to and including 100% (no specific protein or RNA present). It should be noted that even qualitative differences can be represented in quantitative terms if desired. For example, a change in the intracellular localization of a polypeptide can be represented as a change in the percentage of cells showing the original localization.

As used herein "disease recurrence" refers to the development or emergence of cells of a disease, such as a cell proliferative disease (e.g., a tumor), after a treatment that has substantially removed diseased cells. A disease recurrence can be at the same site as the original disease or elsewhere, but will involve accumulation of cells of the same tissue of origin as in the original disease.

As used herein "a cell proliferative disorder" is a condition marked by any abnormal or aberrant increase in the number of cells of a given type or in a given tissue. Cancer is often thought of as the prototypical cell proliferative disorder, yet disorders such as atherosclerosis, restenosis, psoriasis, inflammatory disorders, some autoimmune disorders (e.g., rheumatoid arthritis) are also caused by abnormal proliferation of cells, and are thus examples of cell proliferative disorders. "Abnormally proliferating" or "abnormally growing cells" are cells which lose differentiation markers and/or infiltrate areas of tissue where they are not normally found, and/or express cancer cell markers (biomolecules expressed in significantly larger amounts in cancer cells compared to non-cancerous cells as determined by routine statistical testing to within 95% confidence levels).

As used herein "information about a patient" refers to any information known about an individual (a human or non-human animal) from whom a tissue or cell sample was obtained. The term "patient" does not necessarily imply that the individual has ever been hospitalized or received medical treatment prior to obtaining a tissue sample. The term "patient information" can include, but is not limited to, age, sex, weight, height, ethnic background, occupation, environment, family medical background, the patient's own medical history (e.g., information pertaining to prior diseases, current diseases, diagnostic and prognostic test results, drug exposure or exposure to other therapeutic agents, responses to drug exposure or exposure to other therapeutic agents, results of treatment regimens, their success, or failure, history of alcoholism, drug or tobacco use, cause of death, and the like). The term "patient information" refers to information about a single individual; information from multiple patients provides "demographic information," defined as statistical information relating to populations of patients, organized by geographic area or other selection criteria, and/or "epidemiological information," defined as information relating to the incidence of disease in populations.

As used herein "information relating to" is information which summarizes, reports, provides an account of, and/or communicates particular facts, and in some aspects, includes information as to how facts were obtained and/or analyzed.

As used herein "in communication with" refers to the ability of a system or component of a system to receive input data from another system or component of a system and to provide an output in response to the input data. "Output" can be in the form of data or can be in the form of an action taken by the system or component of the system.

As used herein "an individual" is a single organism and includes humans, animals, plants, multicellular and unicellular organisms.

As used herein a "database" is a collection of information or facts organized according to a data model which determines whether the data is ordered using linked files, hierarchically, according to relational tables, or according to some other model determined by the system operator. The organization scheme that the database uses is not critical to performing the invention, so long as information within the database is accessible to the user through an information management system. Data in the database are stored in a format consistent with an interpretation based on definitions established by the system operator (i.e., the system operator determines the fields which are used to define patient information, molecular profiling information, or another type of information category).

As used herein "a system operator" is an individual who controls access to the database.

As used herein "information management system" refers to a system which comprises a plurality of functions for accessing and managing information within the database. Minimally, an information management system according to the invention comprises a search function, for locating information within the database and for displaying a least a portion of this information to a user, and a relationship determining function, for identifying relationships between information or facts stored in the database.

As used herein "providing access to at least a portion of a database" as defined herein refers to making information in the database available to user(s) through a visual and/or auditory means of communication.

As used herein "through a visual means of communication" includes displaying or providing written text, image(s), or a combination of written and graphical information to a user of the database.

As used herein "through an auditory means of communication" refers to providing the user with taped audio information, or access to another user who can communication the information through speech or sign language. Written and/or graphical information can be communicated through a printed report or electronically (e.g., through a display on the display of a computer or other processor, through email or other electronic messaging systems, through a wireless communications device, via facsimile, and the like). Access can be unrestricted or restricted to specific subdatabases within the database.

As used herein "an exogenous nucleic acid" refers to a nucleic acid which is not naturally found in the genome of an animal or plant.

As used herein "a correlation" refers to a statistically significant relationship determined using routine statistical methods known in the art. For example, in one aspect, statistical significance is determined using a Student's unpaired t-test, considering differences as statistically significant at $p<0.05$.

As used herein a "diagnostic probe" is a probe whose binding to a tissue and/or cell sample provides an indication of the presence or absence of a particular trait. In one aspect, a probe is considered diagnostic if it binds to a diseased tissue and/or cell ("disease samples")in at least about 80% of samples tested comprising diseased tissue/cells and binds to less than 10% of non-diseased tissue/cells in samples ("non-disease" samples). Preferably, the probe binds to at least about 90% or at least about 95% of disease samples and binds to less than about 5% or 1% of non-disease samples.

As used herein "electronic subtraction" refers to a method of comparing a first expressed sequence database with a second expressed sequence database and electronically removing sequences which are in both the first and second database. Methods of electronic subtraction are described in U.S. Pat. No. 5,840,484, for example, the entirety of which is incorporated by reference herein.

As used herein "a probe corresponding to a differentially expressed sequences" is a probe capable of specifically reacting with the sequence such that reactivity of the probe with a sample indicates the presence of the sequence.

Microarrays

As shown schematically in FIG. 1A, a frozen microarray 13 according to the invention comprises a substrate 43 on which a plurality of frozen tissue and/or cell samples are disposed at a plurality of sublocations 13s. Preferably, each sample on the microarray 13 has at least one known biological characteristic (e.g., such as tissue type or cell type or patient source). Microarray samples have substantially intact morphological features, i.e., the samples are not lysed.

The substrate 43 facilitates handling of the microarray 13 during a variety of molecular procedures. Preferably, the substrate 43 is transparent and solvent resistant. Suitable substrates include, but are not limited to: glass; quartz; fused silica or other nonporous substrates; plastic (e.g., polyolefin, polyamide, polyacarylamide, polyester, polyacrylic ester, polycarbonate, polytetrafluoroethylene, polyvinyl acetate, and the like), and the like. Substrates can additionally include one or more of fillers (such as glass fillers); extenders; stabilizers; antioxidants; resins (e.g., celluloid, cellophane, urea, formaldehyde, cellulose acetate, ethylcellulose); and the like. The substrate, while preferably rigid, can also be semi-rigid or flexible (e.g., flexible plastic, nylon or nitrocellulose). Preferably, the substrate is optically opaque and substantially non-fluorescent (e.g., for use in applications where fluorescent labels are used to identify or confirm biological characteristics).

The size and shape of the substrate can be varied. However, preferably, the substrate fits entirely on the stage of a microscope. In one aspect, the substrate is planar; however, in another aspect, the substrate comprises irregularities or cavities.

Figure 1B:
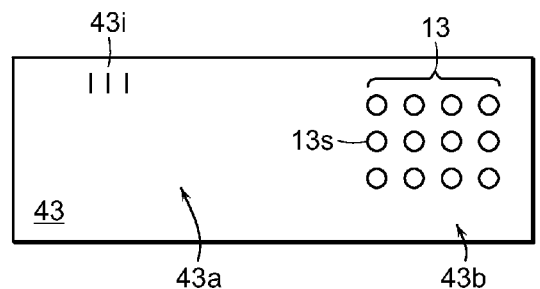
FIG. 1B is a schematic of a profile array substrate according to one aspect of the invention comprising a frozen microarray.
Figure 1C:
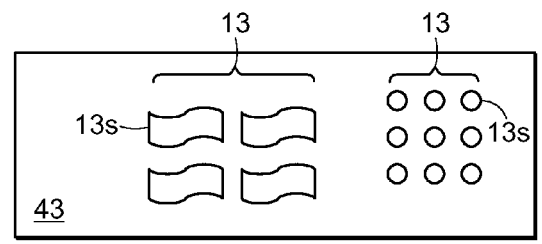
FIG. 1C shows a mixed format microarray comprising a frozen large format array and small format array on a single substrate.

In one aspect, the substrate 43 is a "profile array substrate" designed to accommodate at least a control microarray (e.g., a microarray comprising samples whose reactivity with at least one molecular probe is known) and a test tissue or test cell sample for comparison with the control microarray. As shown in FIG. 1B, such a profile microarray substrate 43 comprises a first location 43a for placing the test sample and a second sublocation 43b comprising the microarray 13. This allows a user to test a test sample and control microarray 13 for the presence or absence of one or more biological characteristics at the same time and under the same conditions such that a side-by side comparison of results can be obtained. Profile microarray substrates 43 are disclosed in U.S. Provisional Application Ser. No. 60/234,493, filed Sep. 22, 2000, the entirety of which is incorporated by reference herein.

In one aspect of the invention, as shown in FIG. 1B, the substrate 43 comprises a location for placing an identifier 43i (e.g., a wax pencil or crayon mark, an etched mark, a label, a bar code, a microchip for transmitting radio or electronic signals, and the like). For example, the identifier can be a microchip which communicates with a processor which comprises, or can access, stored information relating to the identity and address of sublocations 13s on the microarray and/or including patient information regarding the individual from whom the tissue was taken.

Sources of Microarray Samples

In one aspect, the microarray samples are tissue samples. Tissue samples can be obtained from cadavers or from patients who have recently died (e.g., from autopsies). Tissues also can be obtained from surgical specimens, pathology specimens (e.g., biopsies), from samples which represent "clinical waste" which would ordinarily be discarded from other procedures. Samples can be obtained from adults, children, and/or fetuses (e.g., from elective abortions or miscarriages).

Cells also can be obtained to provide one or more samples in the microarray. Cells can be obtained from suspensions of cells from tissues (e.g., from a suspension of minced tissue cells, such as from a dissected tissue), from bodily fluids (e.g., blood, plasma, sera, and the like), from mucosal scrapings (e.g., such as from buccal scrapings or pap smears), and/or from other procedures such as bronchial ravages, amniocentesis procedures and/or leukophoresis. In some aspects, cells are cultured first prior to being made part of the microarray to expand a population of cells to be analyzed. Cells from continuously growing cell lines, from primary cell lines, and/or stem cells, also can be used.

In one aspect, a microarray 13 comprises a plurality of tissues/cells from a single individual, i.e., the microarray represents the "whole body" of an individual. Preferably, a "whole body microarray" according to the invention comprises at least five different types of tissues from a single patient. More preferably, the whole body microarray comprises at least 10 or at least 15 different tissues. Tissues can be selected from the group consisting of skin, neural tissue, cardiac tissue, liver tissue, stomach tissue, large intestine tissue, colon tissue, small intestine tissue, esophagus tissue, lung tissue, cardiac tissue, spleen tissue, pancreas tissue, kidney tissue, tissue from a reproductive organ(s) (male or female), adrenal tissue, and the like. Tissues from different anatomic or histological locations of a single organ can also be obtained, e.g., such as from the cerebellum, cerebrum, and medulla, where the organ is the brain. Some microarrays comprise samples representative of organ systems (i.e., comprising samples from multiple organs within an organ system), e.g., the respiratory system, urinary system, kidney system, cardiovascular system, digestive system, and reproductive system (male or female). In a preferred aspect, a whole body microarray additionally comprises a sample of cells from a bodily fluid of the patient (e.g., from a blood sample).

The microarray 13 also can comprise a plurality of sublocations 13s comprising cells from individuals sharing a trait. For example, the trait shared can be gender, age, pathology, predisposition to a pathology, exposure to an infectious disease (e.g., HIV), kinship, death from the same disease, treatment with the same drug, exposure to chemotherapy, exposure to radiotherapy, exposure to hormone therapy, exposure to surgery, exposure to the same environmental condition (e.g., such as carcinogens, pollutants, asbestos, TCE, perchlorate, benzene, chloroform, nicotine and the like), the same genetic alteration or group of alterations, expression of the same gene or sets of genes (e.g., samples can be from individuals sharing a common haplotype, such as a particular set of HLA alleles), and the like.

Samples can be obtained from an individual with a disease or pathological condition, including, but not limited to: a blood disorder, blood lipid disease, autoimmune disease, bone or joint disorder, a cardiovascular disorder, respiratory disease, endocrine disorder, immune disorder, infectious disease, muscle wasting and whole body wasting disorder, neurological disorders including neurodegenerative and/or neuropsychiatric diseases, skin disorder, kidney disease, scleroderma, stroke, hereditary hemorrhage telangiectasia, diabetes, disorders associated with diabetes (e.g., PVD), hypertension, Gaucher's disease, cystic fibrosis, sickle cell anemia, liver disease, pancreatic disease, eye, ear, nose and/or throat disease, diseases affecting the reproductive organs, gastrointestinal diseases (including diseases of the colon, diseases of the spleen, appendix, gall bladder, and others) and the like. For further discussion of human acme diseases, see *Mendelian Inheritance in Man: A Catalog of Human Genes and Genetic Disorders* by Victor A. McKusick (12th Edition (3 volume set) June 1998, Johns Hopkins University Press, ISBN: 0801857422), the entirety of which is incorporated herein. Preferably, samples from a normal demographically matched individual and/or from a non-disease tissue from a patient having the disease are arrayed on the same or a different microarray to provide controls.

In one aspect, sets of microarrays 13 are provided representing multiple individuals with approximately 30,000 specimens covering at least about 1, 2, 5, 10, 15, 20, 25, 30, 40, or 50, different disease categories, including, but not limited to, any of the disease categories identified above. In some aspects, microarrays comprise samples from individuals have more than one disease condition (e.g., stroke and cardiovascular disease) and from individuals with only one of each of the diseases (e.g., samples from stroke patients without cardiovascular disease and samples from patients with cardiovascular disease but who have not experienced stroke). In some aspects, samples are from individuals with a chronic disease (e.g., such as Crohn's disease) and samples on the array include samples from patients in a remission period as well as samples from patients in an exacerbation period.

In a preferred aspect, a microarray 13 is provided comprising a plurality of sublocations 13s which represent different stages of a cell proliferative disorder, such as cancer. In one aspect, in addition to including samples which comprise the primary target of the disease (e.g., such as tumor samples), the microarray 13 includes samples representing metastases of a cancer to secondary tissues/cells. Preferably, the microarray 13 also comprises normal tissues from the same patient from whom the abnormally proliferating tissue was obtained. In some aspects, at least one sublocation 13s comprises cells from a cell line of cancerous cells (either primary or continuous cell lines). Samples can be homogeneous, comprising a single cell type (e.g., as in a small format or ultrasmall format microarray), or can be heterogeneous, comprising at least one additional type of cell or cellular material in addition to abnormally proliferating cells (e.g., as in large format microarrays where samples are generally larger than 0.6 mm in diameter). For example, the sample can comprise abnormally proliferating cells and at least one of fibrous tissue, inflammatory tissue, necrotic cells, apoptotic cells, normal cells, and the like.

Although in a preferred aspect of the invention, the microarrays 13 comprise human specimens, in one aspect of the invention, specimens from other organisms are arrayed. In one aspect, the microarray 13 comprises tissues from non-human animals which provide a model of a disease or other pathological condition. When the array represents specimens from an animal model of a chronic disease, the microarray can comprise specimens representing different stages of the disease, e.g., such as from animals in a remission period or an exacerbation period. The microarray 13 can additionally, or alternatively, comprise tissues from a non-human animal having the disease or condition which has been exposed to a therapy for treating the disease or condition (e.g., drugs, antibodies, protein therapies, gene therapies, antisense therapies, combinations thereof, and the like). In some aspects, the non-human animals can comprise at least one cell containing an exogenous nucleic acid (e.g., the animals can be transgenic animals, chimeric animals, knockout or knockin animals). Preferably, arrays from non-human animals comprise multiple tissues/cell types from such a non-human animal. In one aspect, tissues/cells at different stages of development are arrayed.

In still further aspects, samples from plants can be arrayed. Preferably, such arrays comprise plants at different stages of their life cycle and/or comprise different types of plant tissues (e.g., at least about five different plant tissues). In one aspect, samples are obtained from plants which comprise at least one cell containing an exogenous nucleic acid (e.g., the plant can be a transgenic plant).

Generating Frozen Microarrays
  Preparing the Donor Block
  Tissue Donor Blocks

In one aspect, a frozen donor tissue block is prepared by obtaining a fresh tissue sample and freezing the sample by quick-freezing in liquid nitrogen or by any other methods known in the art. The donor frozen tissue block can be stored frozen and archived until further use. In a preferred aspect of the present invention, the donor frozen tissue block is embedded in a fast-freezing embedding matrix to facilitate frozen sectioning. Embedding material useful according to the invention is generally a gelatinous liquid which solidifies at about −110° C. to −15° C. and which surrounds the tissue but does not penetrate into the tissue. Examples of suitable embedding materials include, but are not limited to, OCT (O.C.T. Compound, Tissue-TEK$^R$, Torrance, Calif.), Histo-Prep™ Frozen Tissue Embedding Media (Fisher-Brand™, Fisher Scientific, Pittsburgh, Pa.), CRYO-Gel™ (Instrumedics Inc., Hackensack, N.J.), M-1 Embedding Matrix (Shandon, Pittsburgh, Pa.), Cryomatrix™ (Shandon, Pittsburgh, Pa.), and gelatin. A tissue freezing aerosol, such as tetrafluoroethane 2.2, can also be used to facilitate manufacture of a frozen donor tissue block. Preferably, the block is at least about 1 mm thick. Still more preferably, the block is at least about 2–4 mm thick.

Samples are obtained from donor blocks in a process described further below. Essentially, cores of samples of different or the same donor blocks are used to generate microarray blocks. Sampling from the right site of a donor block is critically important for constructing tissue and/or cell arrays. In one aspect, a section of a donor block is obtained and stained with H&E and the stained section is used as a guide to select a region for sampling. For example, a section of interest (e.g., such as a region comprising abnormally proliferating cells) can be marked on the glass portion of the slide (e.g., by circling the area with a waxed pencil) and the slide can be laid over the block to identify the region corresponding to the circled area on the block. Alternatively, a template corresponding to the slide and marked to indicate an area to sample can be laid over the frozen block to identify appropriate coordinates on the block to core. In other aspects, the slide or a template corresponding to the slide can be marked with grids providing a coordinate system which can be used to identify appropriate coordinates on the block.

While in some aspects, staining with a standard tissue or cell stain such as H&E can be suitable to identify cells or tissue areas of interest, in other aspects, sections of the donor block are evaluated for the expression of one or more biological characteristics (e.g., such as the expression of a genotype, transcript, or peptide, polypeptide, or protein of interest) in the sample represented by the section. An area of interest can be identified which expresses or does not express a particular biological characteristic. Coordinates of the area of interest on the section can be identified and the same coordinates can be marked on the donor block as being suitable for sampling.

Cell Donor Blocks

Donor blocks also can be generated which comprise cells rather than tissues. For example, the donor blocks can comprise embedded cells obtained from cell suspensions. Cells used to form the donor blocks can be obtained from cell culture (e.g., from primary cell lines or continuous cells lines), from dissections, from surgical procedures, biopsies, pathology waste samples (e.g., by mincing or otherwise disassociating tissues from these samples), as well as from bodily fluids (e.g., such as blood, plasma, sera, leukophoresis samples, and the like). Cells can also be obtained after one or more purification steps to isolate cells of a particular type (e.g., by dissection, flow sorting, density gradient centrifugation, and the like).

Cells are preferably washed one or more times in a suitable buffer which does not lyse the cell and are collected by centrifugation. After removing substantially all of the buffer, cells are resuspended gently in a volume of fast-freezing embedding material and transferred in the embedding material to a mold, such as a support web or plastic block, for freezing. As above, after the mold is removed, at least one section from the block should be evaluated to verify sample integrity (e.g., to validate the presence of suitable numbers of cells with acceptable morphology and/or to determine that cells express or fail to express one or more biomolecules). Cell donor blocks should comprise at least about one cell and preferably comprise at least about 50, at least about $10^2$, at least about $10^3$, at least about $10^4$, at least about $10^5$, at least about $10^6$, least about $10^7$, and at least about $10^8$ cells Forming the Recipient Block A blank frozen block is prepared which comprises frozen embedding material but no tissue or cell samples. For example, embedding material can be poured into a mold and the mold and embedding material subjected to freezing temperatures (temperatures less than or equal to about −20° C.) until the embedding material hardens. The mold is then removed and the frozen block which remains is checked to insure that there are no air bubbles and shaved (e.g., with a razor blade) to remove irregularities from at least one surface of the block. Molds can be of any size but are preferably about 7–18 mm thick.

To prepare the recipient block for receiving donor tissue samples, a plurality of holes is cored into the recipient block in a process described further below. The size of the hole can vary from less than or equal to about 0.3 mm (e.g., to generate ultrasmall format microarrays), about 6.0 mm (e.g., for small format microarrays) to greater than about 0.6 mm (e.g., about 0.7 mm, about 0.8 mm, about 0.9 mm, about 1.0 mm, about 1.3 mm, about 1.5 mm, about 1.7 mm, about 2.0 mm or greater) (e.g., for large format arrays), and can have a varying geometry. A single recipient block also can comprise a plurality of differently sized holes. Preferably, holes are arranged in rows and columns and are elongated or cylindrical in shape. A recipient block can be cored to provide all the holes desired to receive donor samples at a time, or alternatively, a recipient block can be cored to create a hole, filled with a sample, and then cored to create an additional hole, repeating the process multiple times.

Generating the Microarray Block

Microarray blocks are prepared by placing a tissue sample or cell sample from a donor block in a selected hole until all holes have been filled with the desired sample specimens. While the order of the donor tissues in the microarray block is not critical, in some aspects, donor tissue samples are spatially organized in the microarray block. For example, in one aspect, donor samples represent different stages of disease, such as cancer, and are ordered from least progressive to most progressive (e.g., associated with the lowest survival rates) stage of the disease. In another aspect, donor samples within a microarray 13 are ordered into groups which represent the patients from which the samples are derived. For example, in one aspect, groupings are based molecular profiles of patients (e.g., determined by evaluating donor samples using one or more molecular probes), while in another aspect, groupings are based on treatment approaches, treatment outcome, prognosis, or according to any other scheme that facilitates the subsequent analysis of the samples and the data associated with them.

Information regarding the coordinates of the hole into which a tissue sample is placed and the identity of the tissue sample at that hole is recorded. In one aspect of the invention, data relating to any, or all of, tissue type, stage of development or disease, patient history, family history, diagnosis, prognosis, medication, morphology, concurrent illnesses, expression of molecular characteristics (e.g., markers), and the like, are recorded and stored in a database, indexed according to the location of the tissue in the microarray block. Data can be recorded at the same time that the microarray block is formed, or prior to, or after, formation of the microarray block.

In one aspect, up to about 1200 donor samples are arrayed in an about 40 mm×25 mm block. Preferably, at least about 300–500 samples are arrayed, although fewer samples can also be arrayed so long as at least about two samples are placed in the recipient block.

Tissue Microarrayer

Generation of the microarray block can be partially or fully automated using tissue microarrayers such as the ones described in WO 99/44062, WO 99/44063, and U.S. Pat. No. 6,136,592, the entireties of which are incorporated herein by reference. However, such microarrayers are designed for creating microarray blocks of paraffin-embedded tissues and thus are not optimal for arraying frozen tissue samples.

Figure 2:
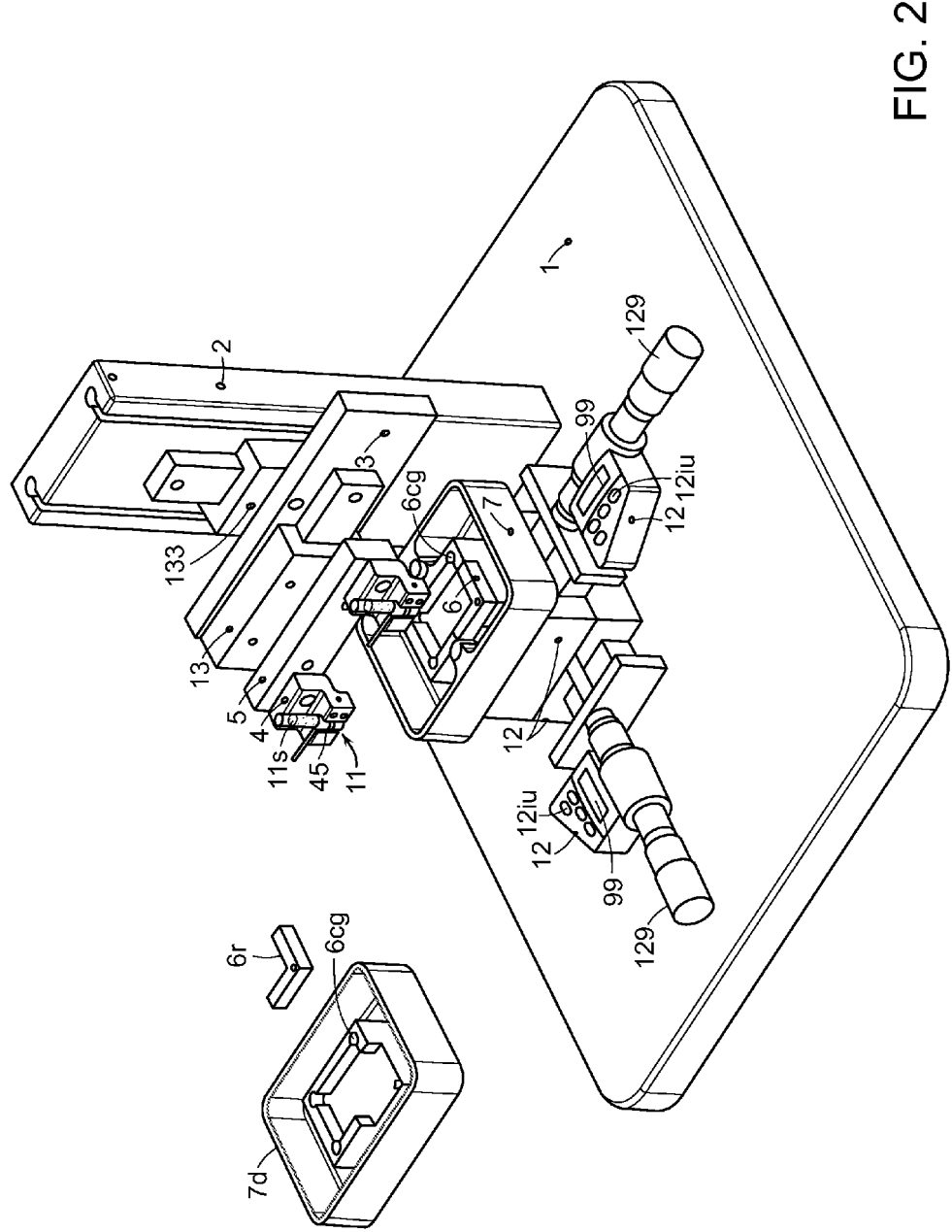
FIG. 2 shows a schematic of a tissue microarrayer device designed to array frozen tissue and/or cell samples according to one aspect of the invention.

Therefore, in a preferred aspect of the invention, microarray blocks are generated using a microarrayer which is designed specifically for the arraying of frozen samples. Such a microarrayer is described in U.S. Pat. No. 6,534,307, filed Feb. 8, 2001, the entirety of which is incorporated by reference herein. As shown in FIG. 2, the frozen tissue microarrayer device comprises at least one platform 12 moveable in an x or y direction relative to a fixed horizontal surface 1 and a cooling chamber 7 for receiving at least one frozen material (e.g., such as a donor block or a recipient block/microarray block) and for maintaining the frozen material in a frozen condition. Preferably, the cooling chamber 7 is moveable with the platform 12, such that when the platform 12 moves in an x-direction, the cooling chamber 12 also moves in an x-direction and when the platform moves in a y-direction, the cooling chamber 7 moves in a y-direction.

The cooling chamber 7 can be cooled in a variety of ways, e.g., by providing the cooling chamber 7 with a source of cold water (e.g., water cooled to 1° C. to 4° C.), a mixture of cold water and ice, or compressed air. In one aspect, the cooling chamber 7 comprises sealed tubing configured to form a jacket of cooling fluid (e.g., water or air) around a block of frozen material. An insulator sheet (not shown) also can be placed between the platform 12 and cooling chamber 7, to minimize heat dissipation from the cooling chamber or heat conduction from the platform 12. In another aspect, the cooling chamber 7 further comprises a retaining chamber 6 for retaining at least one block of frozen material. The retaining chamber 6 is preferably made of an insulating material for maintaining a temperature of from 0° C. to 4° C. or below. In some aspects, the retaining chamber 6 is surrounded by cold water, a mixture of ice and water, or cold air (e.g., from a compressed air source which communicates with the cooling chamber 7), or a jacket through which a cooling fluid circulates.

In one aspect, one or more blocks fits snugly into the retaining chamber 6 with substantially no clearance space between the block(s) and the retaining chamber 6 walls. In this aspect, the retaining chamber 6 comprises one or more corner grooves 6cg, to provide a levering space for an instrument (e.g., a spatula) used to lift the block from the retaining chamber. In another aspect, there is clearance between the block material and the walls of the retaining chamber 6, and the retaining chamber 6 comprises one or more holders for holding block(s) of frozen material in place.

In still another aspect, a section of the retaining chamber, 6r can be removed from the chamber, for ease of grasping the block.

The device further accommodates at least one coring needle 11 comprising a cutting edge for cutting frozen material and a lumen for receiving a core of the cut frozen material. In one aspect, the coring needle 11 is used to cut a core of embedded frozen tissue or cell sample from a block of embedding matrix (e.g., a donor block). The same or a different coring needle 11 is used to cut a core of frozen embedding matrix from a block of an embedding matrix (e.g., a recipient block) which is used to form one or more microarrays, leaving a hole of approximately the same size or a size slightly smaller than the core of sample. The core of frozen tissue is then placed in the hole previously filled by the core of embedding matrix. The process is repeated multiple times until a recipient block comprising a plurality of donor sample cores is generated, i.e., a microarray block is formed.

The shape of the coring needle 11 can vary. In one aspect, the lumen of the coring needle 11 forms a cylindrical space (e.g., for forming a cylindrical core of donor sample). However, other shapes are included within the scope of the invention. In one aspect, the cross-section perpendicular to the longitudinal axis of the coring needle 11 is any of circular, rectangular, polygonal, oval, square, trapezoidal shaped, and the like. Preferably, the coring needle 11 has a uniform cross-section. The size of the core of frozen material can also vary. In one aspect, a core of frozen material of about 1–10 mm in length can be obtained using the coring needle 11. In one aspect, the diameter of the core thus obtained ranges from about 0.3 to about 10.0 mm, about 0.6–10 mm, and preferably about 0.3–2.0 mm.

In one aspect of the invention, the microarrayer device comprises a first and second coring needle 11, the first coring needle 11 (donor coring needle) dedicated to coring tissue samples, the second coring needle 11 (recipient coring needle) dedicated to coring holes in the recipient block. In this aspect, preferably the donor coring needle 11 is slightly larger than the recipient coring needle 11 (e.g., the second coring needle 11 would be able to slidably fit within the first coring needle 11). The lumens of the coring needles 11 are sized such that a tissue sample obtained from a donor block snugly fits in a hole created in the recipient block.

The device further comprises a positioning element 4 for positioning the at least one coring needle 11 over a donor block or recipient block. In one aspect of the invention, the positioning element 4 comprises a recess 4r for receiving a coring needle 11 and a clip (not shown) for securing the coring needle 11 within the recess 4r. In one aspect, the clip is a spring clip, which is held in place on the positioning element 4 by means of a screw. In another aspect, the coring needle 11 comprises a circumferential groove which mates with a ridge, tab, or pin (not shown) in the walls of the recess 4r, while still allowing the coring needle 11 to rotate. This aspect constrains horizontal motion of the coring needle 11 within the positioning element 4, but allows the coring needle 11 to be moved clockwise and counterclockwise to disengage from a block of frozen tissue into which it has cored.

In one aspect, the positioning element 4 is positioned randomly over a tissue sample However, in a preferred aspect, a section of a donor block which is representative of tissue embedded in the entire donor block is examined (e.g., under a microscope as described above) and the coordinates of a sample site desired for inclusion in a microarray are determined (e.g., using a micrometer or gridlines on a microscope slide on which the tissue sample is placed). After suitable coordinates are identified, the donor block is placed in the retaining chamber 6 for coring, is cored, and removed. The recipient block is then placed in the chamber, is cored, and receives the core of tissue sample obtained from the donor block. However, in another aspect, the recipient block is pre-cored and comprises at least one hole for receiving a core of tissue sample.

In one aspect, a coring needle 11 is centered over appropriate coordinates of a donor block as determined by evaluating a representative tissue section from the donor block using a gridded or otherwise marked slide slide. A template comprising gridlines/markings identical to those on the slide is placed on the donor block, using an orienting mark on the donor block to position the template. The template can be the slide that was used to identify desired coordinates or can be a transparent acetate sheet comprising gridlines/markings identical to those on the slide. The retaining chamber 6 comprising the frozen material is moved to center the appropriate coordinates of the donor block under the coring needle 11, e.g., by centering the appropriate template gridlines/markings under the coring needle 11. The retaining chamber 6 can be moved by moving any of the cooling chamber 7, platform(s) 12, or the chamber 6 itself. Alternatively, or additionally, the positioning element 5 comprising the coring needle is moved to center the appropriate coordinates of the donor block under the coring needle 11. The template is then removed, and the coring process is initiated. In one aspect, the device is provided with one or more ocular elements, to allow the user to better visualize features on the template (or slide) when moving the retaining chamber 6 and/or positioning element 4.

Preferably, the retaining chamber 6 is designed to accommodate at least two blocks of frozen materials (e.g., such as a donor and a recipient block), eliminating the need to remove a donor block before coring the recipient block. Further, a plurality of positioning elements 4 can be provided to accommodate a plurality of coring needles. In one aspect, a plurality of positioning elements are coupled to a single holder arm 4, such that movement of the positioning elements 4 in at least an x-direction is coordinated.

Movement of either the retaining chamber 6 or positioning element 4 can be controlled by providing one or more motorized elements (not shown) in communication with the retaining chamber 6 and/or positioning element 4. In one aspect, shown in FIG. 2, for example, movement of both the positioning element 4 and the retaining chamber 6 is controllable by the user either directly or through a processor 99 in communication with the motor(s).

In one aspect, the movement of the retaining chamber 6 is coupled to that of the cooling chamber 7 which is turn is coupled to movement of at least one platform 12. The movement of the platform 12 can be controlled manually, e.g., by using a grasping element 12g (e.g., such as a joystick) coupled the platform 12, or can be mechanically controlled, e.g., by providing a motor in communication with the platform 12, in one aspect, an x-direction platform 12 in communication with an x-direction motor is provided for controlling movement of the cooling chamber 7 in an x-direction, and a y-direction platform 12 in communication with a y-direction motor is provided for controlling movement of the cooling chamber 7 in a y-direction. By providing both platforms, the cooling chamber 7 is able to move in both an x- and y-direction.

In one aspect of the invention, the x- and/or y-direction motors are servo motors which are responsive to signals from a processor (not shown). In another aspect of the invention, the processor is in communication with at least one input unit 12iu into which the user can input desired x- or y- coordinates respectively. Servo motors and control devices are well known in the art and are described, for example, in U.S. Pat. No. 5,194,793 and U.S. Pat. No. 5,194,790, the entireties of which are incorporated by reference herein. Other types of motors, such as drive motors and stepper motors, can also be used (see, as discussed in U.S. Pat. No. 5,194,790, U.S. Pat. No. 5,139,005, and U.S. Pat. No. 5,103,338, the entireties of which are incorporated by reference herein).

In the aspect shown in FIG. 2, for example, movement of the positioning element 4 is also controllable by a user, permitting a further means to precisely position an at least one coring needle 11 relative to a frozen tissue sample or block of embedding matrix. In this aspect, the positioning element 4 is coupled to a x-direction slide 133 which moves in an x-direction upon receiving a mechanical force, either from a user (e.g., by pushing on the slide 133), or from a motorized element (not shown) which is coupled to x-direction slide plate 3. In a further aspect (not shown), an additional degree of freedom of motion is afforded by pivotally connecting the positioning element 4 to the x-direction slide 133. It should be obvious to those of skill in the art, that any of a number of slide elements can be provided, which can be pivotally coupled or fixedly coupled to one or more other slide elements and/or plates.

In the aspect shown in FIG. 2, there are two positioning elements 4 and the movement of both elements is coordinated by coupling both positioning elements 4 to a single positioning element holder 5. However, in another aspect, the ability to move independently can be afforded to each positioning element 4, for example, by pivotally coupling each positioning element 4 to the positioning element holder 5.

The positioning element(s) 4 can be fixed in place once a desired position is reached by providing one or more screw elements (not shown) for screwing one or more slide elements at a given position and/or by providing one or more screw elements for screwing the positioning elements 4 themselves (e.g., such as in the aspect where these are able to pivot about the positioning element holder 5).

Once a donor block and/or recipient block is satisfactorily positioned relative to at least one coring needle 11, the coring process can be initiated. In one aspect, shown in FIG. 2, coring of a block of frozen material which is secured in the retaining chamber 6 is controlled by coupling one face of an x-direction vertical slide 133 (a slide that can move both in an x and z direction) to positioning element holder 5 and another face to a vertical slide plate 2. In this aspect, vertical translation of the vertical slide 133 (e.g., in a z-direction), in turn, moves the positioning element 4 in a z-direction. When the positioning element 4 is directed downwards, a linear force is exerted against the cutting edge of the coring needle 11 secured in the recess 4r of the positioning element 4. This force translates into a cutting action by the coring needle 11, driving a core of frozen material (e.g., tissue or embedding matrix) into the lumen of the coring needle 11. Vertical movement upwards pulls the coring needle 11 with its core of frozen material out of the frozen block; as the coring needle 11 is moved upwards, its ability to rotate clockwise and/or counterclockwise also aids in disengaging it from the block of frozen material.

In one aspect, where a single coring needle 11 is provided and donor and recipient blocks are placed sequentially in the retaining chamber 6, after placement of a donor block and coring by the coring needle 11, the coring needle 11 with its core of tissue sample is moved via the positioning element 4 to a "parking position" (e.g., by pushing the holder 5 in an x-direction or z-direction away from the retaining chamber, or by pivoting the positioning element 4 about a pivot point on the holder 5, swinging the positioning element away from the donor block). The donor block is then removed from the retaining chamber 6, and a recipient block (which has been pre-cored) is placed in the chamber 6. The positioning element 4 is positioned over an appropriate hole in the recipient block and the core of tissue is pushed or ejected from the coring needle 11 into the recipient block. The positioning element 4 is again moved aside while the recipient block is removed and a new donor block placed in the retaining chamber 6.

In another aspect, a donor block is placed on a removable bridge (not shown) on top of a pre-cored recipient block, and when the donor tissue is obtained, the bridge with the donor block is displaced (e.g., manually or by coupling the bridge to a swing arm), making the recipient block accessible to the coring needle 11. The coring needle 11 is then moved vertically downward to just above a hole in the recipient block, the recipient block having been previously properly positioned relative to the position of the coring needle 11. The tissue core is then expelled from the coring needle 11 into the hole in the recipient block without having to take time to position the recipient block.

In a preferred aspect, shown in FIG. 2, for example, the device provides at least two coring needles 11, each secured in a different positioning element 4. In this aspect, a first coring needle 11 is dedicated for coring donor blocks, while a second coring needle 11 is dedicated for coring recipient blocks. The retaining chamber 6 is sized to receive both a donor block and recipient block simultaneously.

In still a further aspect, a donor block is kept cooled within an insulated cooling chamber 7d outside of the device while the recipient block is processed in a cooling chamber 7. The cooling chamber 7 can then be removed from the device while cooling chamber 7d is seated on platform 12 for processing the donor block.

The movement of both the first and second coring needle 11 can be coordinated. For example, in one aspect, as shown in FIG. 2, both the first and second positioning elements are coupled to a single x-direction slide 133, such that each positioning element 4 moves in identical increments. In one aspect, when the first coring needle 11 (the donor coring needle 11) moves to a first position over selected coordinates on the donor block, the second coring needle 11 moves to a second position over identical coordinates on the recipient block. In this aspect, while the first coring needle 11 cores a tissue sample from the donor block the second coring needle 11s coring a core of embedding matrix from the recipient block.

In one aspect, a donor coring needle 11 comprising a core of donor tissue is moved from a first position over a donor block to a second position over a recipient block, e.g., by sliding the holder 5 in an x-direction, or by providing a slide rail on the holder 5, on which the positioning element 4 can itself be slid. The recipient coring needle 11 comprising a core of embedding matrix is then pushed away from the recipient block by sliding and/or pivoting the positioning element 4 securing the recipient coring needle 11. In this aspect, the core of donor tissue is ejected from the donor coring needle 11 into the hole in the recipient block created by the recipient coring needle 11 while the core of embedding matrix is removed from the recipient coring needle 11. A new donor block is then placed in the retaining chamber 6, and the first and second coring needle 11's are returned to the first and second position, respectively (i.e., positioning the first coring needle 11 over the new donor block and the second coring needle 11 back over the recipient block), and the process is repeated.

Placement of blocks within, and removal from, the retaining chamber 6 can be mediated in a variety of ways. In one aspect, a block can be gently pried from the retaining chamber 6, e.g., by using a spatula to lift the edges of the block. In another aspect, the bottom of the retaining chamber 6 is controllably magnetized (e.g., by a processor in communication with the microarrayer), and a magnetic element is placed on the bottom of the frozen block (e.g., via an adhesive backing). When a frozen block is to be removed, the magnetic field is turned off, thereby releasing the block. In still another aspect of the invention, the base of the retaining chamber 6 comprises a conveyer belt, or movable platform, and blocks are mechanically moved from one position to another. This process can be controlled by a processor in communication with the microarrayer device. However, in a further aspect of the invention, blocks also can be placed into the retaining chamber 6 manually and positioned using attachment screws. In this aspect, a block is held in place in the retaining chamber by a plurality of location bars held in position by magnets built into the arrayer.

In another aspect of the invention, the retaining chamber 6 is sized to accommodate a waste chamber (not shown) at a third position within the retaining chamber 6. In this aspect, rather than being placed in a parking position when the first coring needle 11 is positioned over the recipient block, the second coring needle 11 is positioned over the waste chamber and the core of embedding matrix within the second coring needle 11 is deposited in the waste chamber as the first coring needle 11 deposits the core of tissue sample in the recipient block.

Preferably, the spacing between the centers of two adjacent donor specimens in the array ranges from about 0.65 mm to about 1 mm, and preferably about 0.8 mm, given a coring needle having a diameter of about 0.6 mm, i.e., providing a spacing which is approximately equal or larger than the diameter of the donor sample. However, it should be obvious to those of skill in the art that the distance between samples is not critical so long as the separate identity of samples can be maintained. Preferably, a suitable distance is left at the edges of the microarray block to avoid cracking of the frozen block. For example, in one aspect, microarray blocks are generated comprising margins of at least about 1–3 mm, and preferably from about 2.5–3 mm of frozen embedding material.

More than two coring needles 11 (and more than two positioning elements 4) also can be provided. In one aspect, a first, second, and third coring needle 11 are provided, the first being slightly larger than the second, the second being slightly larger than the third. In this aspect, the user can choose to use the first coring needle 11 as the donor needle and the second coring needle 11 as the recipient needle, or can choose to use the second coring needle 11 as the donor needle and the third coring needle 11 as the recipient needle. Thus, the user can create microarray blocks comprising different-sized tissue cores using a single microarrayer device according to the invention. In one aspect, a microarray is generated comprising a plurality of tissues, each tissue having any of a plurality of selectable sizes. In another aspect, a single microarray block is generated which comprises differently sized cores.

In one aspect, the coring process is facilitated by the use of one or more stylets 11s's to push frozen tissue or embedding matrix out of the lumen of the coring needle 11. In one aspect, the coring needle 11 is in communication with a stylet 11s which can be slideably moved in and out of the lumen of the coring needle 11. The movement of the stylet 11s can be manually controlled or powered by mechanical (e.g., wind-up), electrical, electromagnetic, pneumatic or hydraulic mechanisms.

Figure 3A:
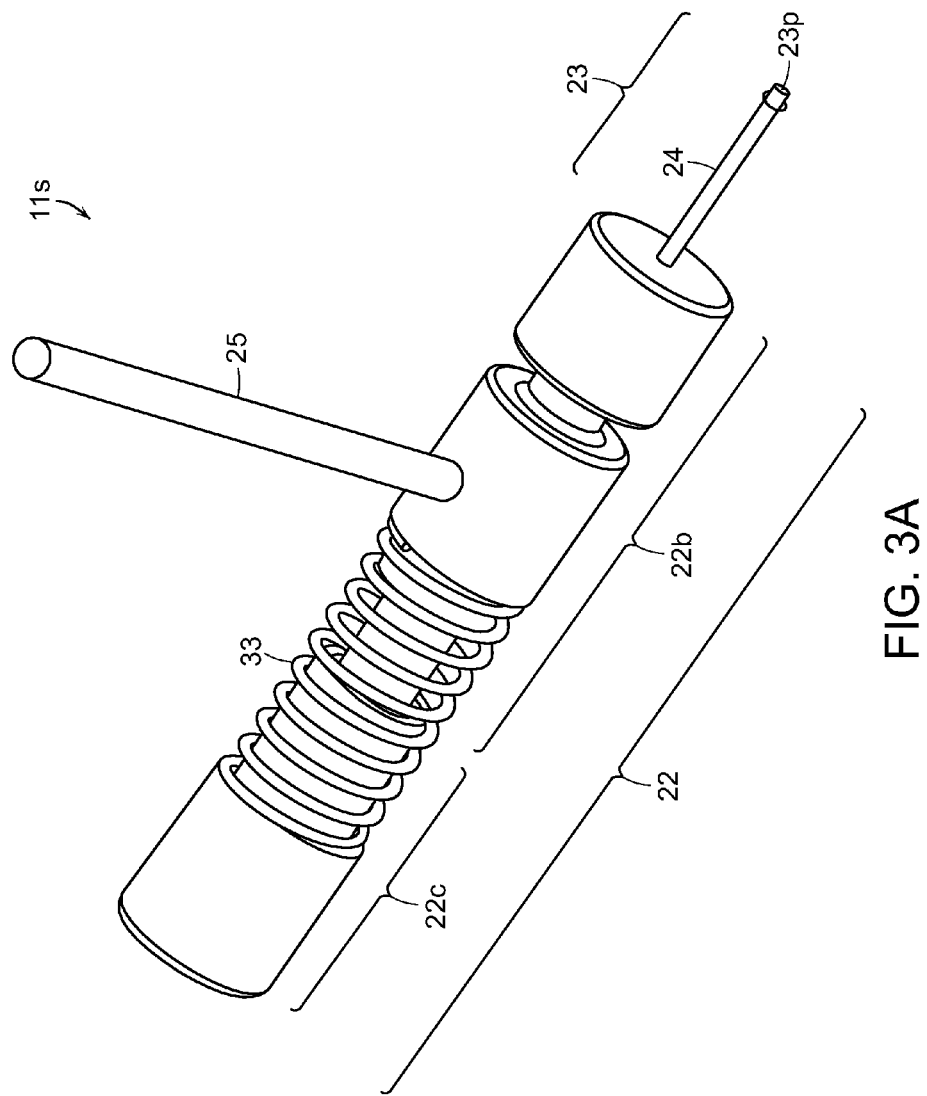
FIGS. 3A and B show different schematic views of a stylet designed to be used in conjunction with the device of FIG. 2 to array frozen tissues and/or cell samples according to one aspect of the invention.

A variety of stylets 11s's can be used. In one aspect (shown in FIG. 3A) the stylet 11s comprises a stylet needle 23 having a pushing surface 23p and a connecting end (not shown) for connecting to a stylet body 22. The stylet needle 23 is stabilized within the stylet body 22 by a stylet tube 24 into which the stylet needle 23 can slideably fit. In one aspect, the stylet body 22 comprises two separable units, a stylet base 22b and a stylet cap 22c, each separated from each other by a resilient element 33. Both the stylet base 22b and cap 22c stabilize and substantially prevent axial movement of the needle 23 within the stylet body 22. When linear force is provided to the stylet needle 23 (e.g., by pushing on the stylet cap and/or by downward movement of the stylet controlled by the stylet driver), the pushing surface 23p of the stylet needle 23 contacts frozen donor sample and/or embedding matrix within the lumen of the coring needle 11 and ejects the material from the coring needle 11 (into the hole of a recipient block in the case of a donor sample, or into a waste receptacle, in the case of embedding matrix from the recipient block). The release of force on the stylet cap 22c creates a recoil force which is amplified through the resilient element 33, driving the stylet upwards again.

In a preferred aspect, a stylet 11s is used which is resistant to the impact of repetitively contacting frozen tissue or frozen embedding media. A stylet 11s is preferably used which is tailored for use in generating frozen tissue microarrays (see, e.g., as shown in FIG. 3). Such a stylet 11s is designed to optimally remove embedding material (with or without tissue/cells) from the coring needle 11 without melting the embedding media upon contact, thereby preventing the coring needle 11 from becoming clogged. In a preferred aspect of the invention, the stylet 11s can be used at least about one hundred times to remove tissue and/or embedding material from a coring needle 11. Still more preferably, the stylet 11s can be reused at least about 500 times, or at least about 1000 times.

The stylet needle 23 preferably has one or more of the following properties: impact resistance, moisture resistance, abrasion resistance, chemical resistance (e.g., solvent resistance), static resistance, corrosion resistance; shatter resistance, static resistance, ability to maintain temperatures from −80° C. to 4° C., and combinations thereof.

In one aspect, the stylet needle 23 comprises stainless steel; however, other suitable materials include, but are not limited to: acetal (e.g., Delrin®, Celcon®, Ensital®); acrylic (e.g., Acrylite®, Plexiglas®, Lucite®, Staticon®); Acrylic-PVC Alloys; Acrylonitrile-Butadiene-Styrenre (Cycolac®); FLUOROPLASTICS-Teflon (Teflon,® Kel-F,® Kynar,® Rulon,® Tefzel®); POLYCARBONATE (Lexan®, Hyzod®, Cyrolon®, Staticon®); POLYETHERETHERKETONE PEEK (VicTrex®); POLYETHERIMIDE (Ultem®); POLYOLEFINS Polyethylenes & Polypropylene (UHMW®) & Polyslick®502; POLYURETHANE (Versathane®, Isoplast®); POLYVVINYL CHLORIDE (PVC). The stylet needle 23 portion of the stylet 11s can be obtained from commercial sources, such as Precision Punch & Plastics (6102 Blue Circle Drive Minnetonka, Minn. 55343; www.precisionpunch.com). In one aspect, at least the pushing surface 23p, comprises a non-stick surface, such as polypropylene, teflon, nylon, polyethylene, including derivatives or combinations thereof.

The dimensions of the stylet needle 23 can generally vary and are selected such that the diameter of the stylet needle 23 is slightly smaller than the diameter of the coring needle 11 with which it will be used so that it can slideably fit within the coring needle. In one aspect the stylet needle 23 is cylindrical; however, the stylet needle 23 can be other shapes which conform to different shaped lumens of coring needles (e.g., rectangular, oval, polygonal and like). In one aspect, the stylet needle 23 comprises a uniform cross-section; however, in another aspect the pushing surface 23p of the stylet needle 23 conforms to the shape of the coring lumen of the coring needle 11 for a slideable fit within the coring lumen but comprises a varying and smaller diameter cross-section for the remainder of its length.

In a preferred aspect, the stylet needle 23 is protected from breakage by being supported and is at least partially enclosed within a stylet tube 24 (shown in FIG. 3B) for fitting the stylet needle 23 within the stylet body 22 and preventing rotation of the needle 23 within the tube 24. In one aspect of the invention, the stylet tube 24 comprises stainless steel, such as $316^{th}$ stainless 21- and 23-gauge stainless steel. The support function of the stylet tube 24 is especially desirable when frozen tissues are being arrayed, given a generally higher pushing force needed to push frozen embedding matrix and/or frozen tissue out of the coring needle 11 of the arrayer which causes the needles of the prior art to break frequently which necessitates stopping the arraying process to replace the stylet 11s.

Figure 3B:
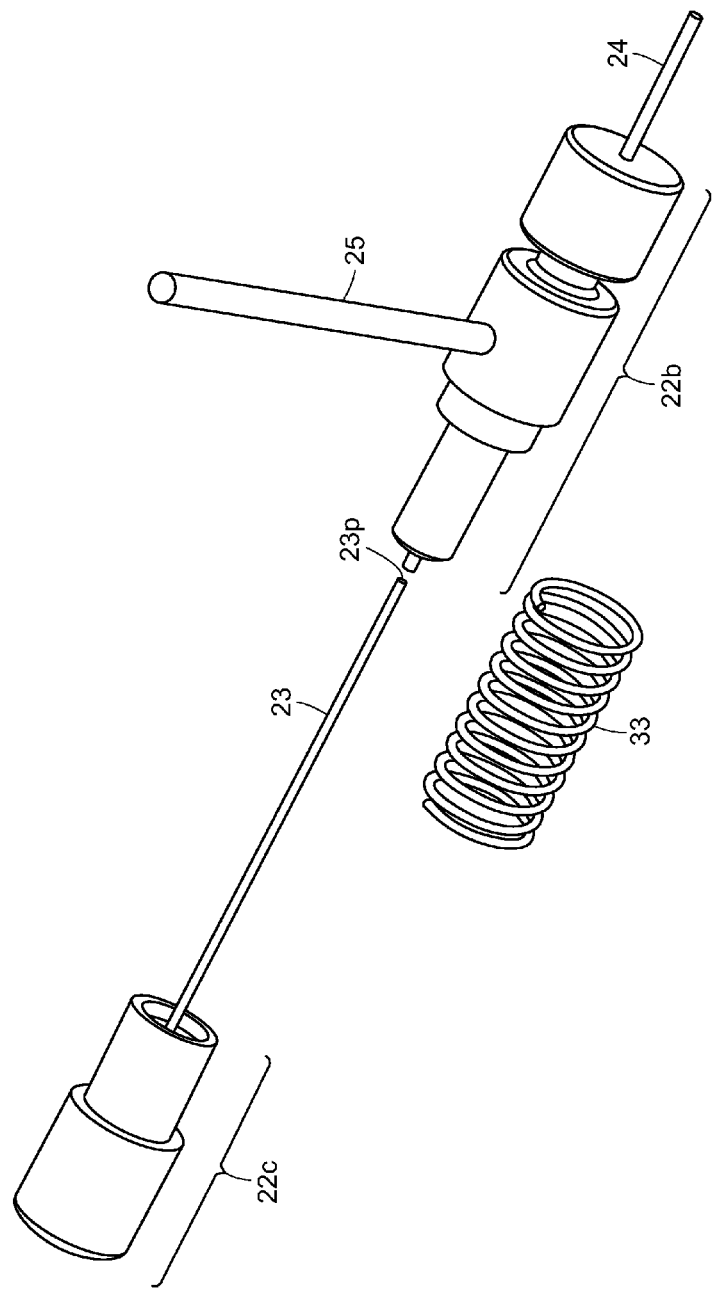
FIG. 3B shows the components of the stylet.

The stylet body 22 reinforces this support function. FIG. 3B shows the placement of the stylet needle 23 within the stylet body 22. In one aspect of the invention, the stylet body 22 comprises polypropylene suitable plastic that will withstand low temperature impact forces. For example, suitable plastics include vinyles, thermoplastic elastomers, urethanes, or low-density olefins; polyolefins, polyesters, acrylics, polyamides, polyamid-imides, polyarylaulfones, polycarbonates, polyetherimides, polyethersulfones, polyetheretherketones, polyoxymethylyenes, polytetrafluoroethylenes, polystyrenes, polyurethanes; oriented or nonoriented polyethylene terephthalate, polypropylene, and blends, thereof. In one aspect, the stylet body 22 comprises mineral reinforced polypropylene which enhances the stiffness of the stylet body 22, such as RTP 136 mineral reinforced polypropylene from Imagineering Plastics®. In another aspect of the invention, the stylet body 22 comprises brass, such as 424 naval brass.

In one aspect, the movement of the stylet 11s is controlled by a stylet driver (not shown) it which is in communication with the stylet 11s and which responds to signals from a processor. The stylet body 22 provides a surface for connection with a stylet driver or other actuation means for moving the stylet. The actuation means can be electric, mechanical, or manual. When the actuation means is electrical, the stylet 11s preferably comprises at least a portion of an electrically conductive material, to allow the user to monitor and control movement of the stylet 11s. The stylet 11s can also comprise a grasping element or handle 25 to allow the user to manipulate the stylet 11s without contacting any surfaces (e.g., 23p) which contact donor sample or embedding media. The handle 25 also facilitates manual removal of the stylet 11s from the automatic tissue arrayer.

In one aspect, coordination of the movement of the stylet 11s with the movement of the coring needle 11 is used to control the depth of coring. In a manual process, contacting of blocks of frozen material by the coring needle 11 is detected/controlled visually and/or by touch. For example, the position of the coring needle 11 and/or the stylet 11s can be monitored using a micrometer with an adjustable depth stop and the needle 11 can pushed downward by hand using the depth stop as a means to block excessive downward motion of the needle 11. Once the coring needle 11 has penetrated a desired distance (e.g., about 0.5–1 mm above the surface of the floor of the retaining chamber 6), the handle 25 of the stylet is used to rotate the coring needle 11 approximately 45° C.; the release of downward pushing pressure on the stylet 11s, creating a reactive backwards linear force which pulls the coring needle 11 upwards.

In other aspects, where the microarrayer device operates automatically or semi-automatically, a processor is provided in communication with a detector which is placed in proximity to the retaining chamber 6 (not shown). The detector is capable of detecting optical information relating to the position of the surface of block(s) positioned beneath the coring needle(s) 11. The detector communicates this information in the form of signals to the processor, which in turn communicates with one or more motors coupled to the positioning element 4 and/or slider elements (e.g., 133) of the device.

In one aspect, the stylet needle 23 of the stylet 11s protrudes a fixed and known distance from the bottom of the cutting edge of the coring needle 11, for example when the lumen of the coring needle 11 is empty. The stylet 11s, which is slideable in the lumen of the coring needle 11, contacts the block but does not penetrate. When the coring needle 11 moves downwards (e.g., through the action of a z-direction slide), the stylet 11s slides upwards within the lumen of the coring needle 11, pushed upwards by the core of frozen material received by the lumen of the coring needle. Upon receiving an ejection signal (e.g., from a stylet driver in communication with a processor) (not shown), the stylet needle 23 moves downwards through the lumen of the coring needle 11 to eject the core of frozen material.

In one aspect of the invention, motion of the stylet 11s is detected by a detector (such as one responsive to optical or electromagnetic signals from the stylet) and signals from the detector are routed to a processor which in turn sends signals to one or a plurality of slide elements to which the stylet driver is coupled, thereby controlling the motion of the stylet.

Additional methods of monitoring and controlling the movement of a stylet relative to a coring needle are described in U.S. Pat. No. 6,103,518, the entirety of which is incorporated by reference herein.

Forming the Microarray

Once the recipient block is filled with a desired number of donor sample cores (thereby becoming a microarray block), it is preferably warmed for a brief period (e.g., about 1–5 minutes at room temperature) to allow the donor sample cores from the donor blocks to adhere to the walls of the holes in the frozen embedding matrix. The block can then be re-frozen for storage or for sectioning. Sections from the microarray block are placed on suitable substrates, thereby generating a plurality of substantially identical microarrays. Preferably, each microarray block generates between at least about 150 to at least about 300 sections of from about 2 µm–20 µm thick. More preferably, sections are between from about 4 µm–12 µm thick. Microarray blocks can be sectioned using a sectioning device known in the art (e.g., such as a cryotome) which manually or automatically slices embedded material at temperatures at or below −20° C.

In one aspect, a frozen tissue microarray is prepared by slicing a section of the frozen microarray block (i.e., cutting transversely from the microarray block with respect to the longitudinal axis of the block) and allowing the section to fall on a substrate, such as a glass slide, without crumpling. However, in a preferred aspect, an adhesive film is placed on a surface of the microarray block both to keep the section flat after it is sliced from the block and to provide a surface on which to more easily move the section to the substrate without tearing or wrinkling the section. In this aspect, the block can be kept at −20° C. throughout the entire sectioning procedure or can be pre-warmed for about 10–15 minutes at about 37° C. prior to sectioning to promote adherence of the sectioned microarray block to the tape, after which the section of the microarray block can be re-frozen to temperatures at or below about −20° C. The section on its adhesive backing is then transferred to a substrate (e.g., such as a glass slide), section side-down, and the adhesive film is peeled away from the section. Alternatively, the section can be transferred adhesive film side-down to an adhesive coated slide, thereby adhering the tissue to the slide.

The section, now stably associated with the substrate 43, comprises the microarray 13. The microarray 13 can be stored for future use at temperatures at or below about −20° C. or can be used immediately (e.g., after one or more fixation steps). Adhesive films and adhesive-coated slides are both obtainable from Instrumedics, Inc., Hackensack, N.J. (see, e.g., CryoJan™ Tape Transfer System).

Methods of Using Frozen Microarrays

Frozen microarrays prepared according to the present invention can be used for rapid parallel analyses of tissue and/or cell samples. For example, at least about 200–500 consecutive array sections can be cut from a microarray block to perform the same or different analyses on the same array of tissue samples using a variety of different molecular probes.

Molecular Probes

Antibodies

Antibodies specific for a large number of known antigens are commercially available. Alternatively, or in the case where the expression characteristics of an uncharacterized biomolecule, such as a polypeptide, is to be analyzed, one of skill in the art can raise their own antibodies, using standard techniques.

In order to produce antibodies, various host animals are immunized by injection with the growth-related polypeptide or an antigenic fragment thereof. Useful animals include, but are not limited to rabbits, mice, rats, goats, and sheep. Adjuvants can be used to increase the immunological response to the antigen. Examples include, but are not limited to, Freund's adjuvant (complete and incomplete), mineral gels such as aluminum hydroxide, surface active substances such as lysolecithin, pluronic polyols, polyanions, peptides, oil emulsions, keyhole limpet hemocyanin, dinitrophenol, and adjuvants useful in humans, such as BCG (bacille Calmette-Guerin) and *Corynebacterium parvum*. These approaches will generate polyclonal antibodies.

Monoclonal antibodies specific for a polypeptide can be prepared using any technique that provides for the production of antibody molecules by continuous cell lines in culture. These include, but are not limited to, the hybridoma technique originally described by Kohler and Milstein, 1975, *Nature* 256: 495–497, the human B-cell hybridoma technique (Kosbor et al., 1983, *Immunology Today* 4: 72; Cote et al., 1983, *Proc. Natl. Acad. Sci. USA*. 80: 2026–2030) and the EBV-hybridoma technique (Cole et al., 1985, *In Monoclonal Antibodies and Cancer* Therapy, Alan R. Liss, Inc., pp. 77–96). In addition, techniques developed for the production of "chimeric antibodies" (Morrison et al., 1984, *Proc. Natl. Acad. Sci. USA* 81:6851–6855; Neuberger et al., 1984, *Nature* 312: 604–608; Takeda et al., 1985, *Nature* 314: 452–454) by splicing the genes from a mouse antibody molecule of appropriate antigen specificity together with genes from a human antibody molecule of appropriate biological activity can be used. Alternatively, techniques described for the production of single chain antibodies (see, e.g., U.S. Pat. No. 4,946,778) can be adapted to produce growth-related polypeptide-specific single chain antibodies. The entireties of these references are incorporated by reference herein.

Antibody fragments which contain specific binding sites of a growth-related polypeptide can be generated by known techniques. For example, such fragments include, but are not limited to, $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed (Huse et al., 1989, *Science* 246: 1275–1281) to allow rapid and easy identification of monoclonal Fab fragments with the desired specificity to a growth-related polypeptide. An advantage of cloned Fab fragment genes is that it is a straightforward process to generate fusion proteins with, for example, green fluorescent protein for labeling.

Antibodies, or fragments of antibodies can be used to quantitatively or qualitatively detect the presence of growth-related polypeptides or conserved variants or peptide fragments thereof. For example, immunofluorescence techniques employing a fluorescently labeled antibody coupled with light microscopic, or fluorimetric detection can be used.

Allele-Specific Antibodies and Modification-Specific Antibodies

In preferred embodiments, antibodies are used which are specific for specific allelic variants of a protein or which can distinguish the modified from the unmodified form of a protein (e.g., such as a phosphorylated vs. an unphosphorylated form, a glycosylated vs. an unglycosylated form of a polypeptide, an adenosylated vs. unadenosylated form of a polypeptide). For example, peptides or polypeptides, comprising protein allelic variations can be used as antigens to screen for antibodies specific for these variants. Similarly modified peptides, polypeptides, or proteins can be used to screen for antibodies which bind only to the modified form of the protein and not to the unmodified form. Methods of making allele-specific antibodies and modification-specific antibodies are known in the art and described in U.S. Pat. No. 6,054,273; U.S. Pat. No. 6,054,273, U.S. Pat. No. 6,037,135; U.S. Pat. No. 6,022,683; U.S. Pat. No. 5,702,890; U.S. Pat. No. 5,702, 890; and in Sutton et al., *J. Immunogenet.* 14(1): 43–57 (1987), for example; the entireties of which are incorporated by reference herein.

Nucleic Acid Probes

Nucleic acid probes are also useful to correlate the differential expression of genes with particular traits (e.g., such as cancer or other diseases). In one aspect, the sequence of a gene which is known to be associated with disease is used to generate a probe or primer for use in the present invention. Means for detecting specific DNA sequences within genes are well known to those of skill in the art. In one aspect, oligonucleotide probes chosen to be complementary to a selected subsequence within the gene can be used.

Methods of labeling nucleic acids are well known to those of skill in the art. Preferred labels are those that are suitable for use in in situ hybridization (ISH) or fluorescent in situ hybridization (FISH). In one aspect, nucleic acid probes are detectably labeled prior to hybridization with a tissue sample. Alternatively, a detectable label which binds to the hybridization product can be used. Labels for nucleic acid probes include any composition detectable by spectroscopic, photochemical, biochemical, immunochemical, or chemical means and include, but are not limited to, radioactive labels (e.g. $^{32}$P, $^{125}$I, $^{14}$C, $^{3}$H, and $^{35}$S), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. Dynabeads TM), chemiluminescent labels, and the like. Examples of labels which are not directly detected but are detected through the use of directly detectable label include biotin and dioxigenin as well as haptens and proteins for which labeled antisera or monoclonal antibodies are available.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

Labels can be coupled to nucleic acid probes in a variety of means known to those of skill in the art. In some aspects the nucleic acid probes are labeled using nick translation or random primer extension (Rigby, et al., *J. Mol. Biol* 113: 237 (1977) or Sambrook et al., 1989, *In Molecular Cloning: A Laboratory Manual*, Cold Spring Harbor Laboratory, Cold Spring Harbor, N.Y., the entireties of which are incorporated by reference herein).

Alternatively, sequences or subsequences of donor samples within a microarray can be amplified by a variety of DNA amplification techniques (e.g., polymerase chain reaction, ligase chain reaction, transcription amplification, etc.) prior to detection using a probe. Amplification of nucleic acid sequences increases sensitivity by providing more copies of possible target subsequences. In addition, by using labeled primers in the amplification process, the sequences are labeled as they are amplified.

Aptamer Probes

Aptamer probes are also encompassed within the scope of the invention, e.g., to label molecules which are not readily bound by nucleic acids using Watson-Crick binding or by antibodies. Methods of generating aptamers are known in the art and described in U.S. Pat. No. 6,180,406, U.S. Pat. No. 6,051,388, Green et al., 2001, *Biotechniques* 30(5): 1094–6, 1098, 1100; and Srisawat, 2001, RNA 7 (4): 632–41, for example, the entireties of which are incorporated by reference herein. Aptamers can generally be labeled as described above with reference to nucleic acid probes.

Molecular Profiling

In one aspect, a frozen microarray is contacted with a molecular probe (e.g., an antibody, nucleic acid, and/or aptamer probe) reactive with a biomolecule and the reactivity of the molecular probe is measured to provide an indication of the presence, absence, or form of the biomolecule. Reactivity can be any of: binding, cleavage, processing, and/or labeling, and the like. Preferably, reactivity of the molecular probe with test samples in the microarray is compared with reactivity of the molecular probe with one or more control samples on the same or a different microarray comprising a known amount and/or form of the biomolecule. Molecular profiling can be performed using a variety of techniques, such as immunohistochemistry, in situ hybridization, and the like, in parallel or simultaneously.

Immunohistochemistry (IHC)

In one aspect, the biomolecule of interest being profiled is an antigen. In situ detection of an antigen can be accomplished by contacting a microarray with a labeled antibody that specifically binds the antigen. For example, antibodies can be detectably labeled by linkage to an enzyme for use in an enzyme immunoassay (EIA) (Voller, 1978, *Diagnostic Horizons* 2:1–7, Microbiological Associates Quarterly Publication, Walkersville, Md.); Voller et al., 1978, *J. Clin. Pathol.* 31:507–520; Butler, 1981, *Meth. Enzymol.* 73: 482–523). The enzyme which is linked to the antibody will react with an appropriate substrate, preferably a chromogenic substrate, in such a manner as to produce a chemical moiety which is detectable, for example, by spectrophotometric, fluorimetric or visual means. Examples of enzymes useful in the methods of the invention include, but are not limited to peroxidase, alkaline phosphatase, and RTU AEC.

Detection of bound antibodies can alternatively be performed by radiolabeling antibodies and detecting the radiolabel. Following binding of the antibodies and washing, the samples can be processed for autoradiography to permit the detection of label on particular cells in the samples.

In one aspect, antibodies are labeled with a fluorescent compound. When the fluorescently labeled antibody is exposed to light of the proper wavelength, its presence can be detected due to fluorescence. Many fluorescent labels are known in the art and can be used in the methods of the invention. Preferred fluorescent labels include fluorescein, amino coumarin acetic acid, tetramethylrhodamine isothiocyanate (TRITC), Texas Red, Cy3.0 and Cy5.0. Green fluorescent protein (GFP) is also useful for fluorescent labeling, and can be used to label non-antibody protein probes as well as antibodies or antigen binding fragments thereof by expression as fusion proteins. GFP-encoding vectors designed for the creation of fusion proteins are commercially available.

The primary antibody (the one specific for the antigen of interest) can alternatively be unlabeled, with detection based upon subsequent reaction of bound primary antibody with a detectably labeled secondary antibody specific for the primary antibody. Another alternative to labeling of the primary or secondary antibody is to label the antibody with one member of a specific binding pair. Following binding of the antibody-binding pair member complex to the sample, the other member of the specific binding pair, having a fluorescent or other label, is added. The interaction of the two partners of the specific binding pair results in binding the detectable label to the site of primary antibody binding, thereby allowing detection. Specific binding pairs useful in the methods of the invention include, for example, biotin:avidin. A related labeling and detection scheme is to label the primary antibody with another antigen, such as digoxigenin. Following binding of the antigen-labeled antibody to the sample, detectably labeled secondary antibody specific for the labeling antigen, for example, anti-digoxigenin antibody, is added which binds to the antigen-labeled antibody, permitting detection.

The staining of tissues/cells for detection of antibody binding is well known in the art, and can be performed with molecular probes including, but not limited to, AP-Labeled Affinity Purified Antibodies, FITC-Labeled Secondary Antibodies, Biotin-HRP Conjugate, Avidin-HRP Conjugate, Avidin-Colloidal Gold, Super-Low-Noise Avidin, Colloidal Gold, ABC Immu Detect, Lab Immunodetect, DAB Stain, ACE Stain, NI-DAB Stain, polyclonal secondary antibodies, biotinylated affinity purified antibodies, HRP-labeled affinity purified antibodies, and/or conjugated antibodies.

In one aspect, immunohistochemistry is performed using an automated system such as the Ventana ES System and Ventana gen$^{II}$™ System (Ventana Medical Systems, Inc., Tucson, Ariz.). Methods of using this system are described in U.S. Pat. No. 5,225,325, U.S. Pat. No 5,232,664, U.S. Pat. No 5,322,771, U.S. Pat. No 5,418,138, and U.S. Pat. No 5,432,056, the entireties of which are incorporated by reference herein.

In some aspects, an immunohistochemical assay can be combined with an evaluation of nucleic acids of samples on a microarray. For example, after immunobistochemistry, tissue cores corresponding to samples on the array can be obtained (e.g., from donor blocks) to provide nucleic acid samples for analysis. In one aspect, a sample of a tissue core is deposited in a plastic tube, and DNA and/or RNA extracted using means known in the art. For example, the amount of DNA from a single 0.6 mm diameter tissue core is usually enough for at least 50 PCR reactions. If more DNA is required, for example, for comparative genomic hybridization methods, additional samples can be collected and stored in the same tube. Thus, it can be useful to collect one sample for nucleic acid extraction, and place an adjacent sample into an array block. This sample can then be used for histology verification, ISH or FISH (described further below), additional immunohistochemistry, or it can be stored in an array block for future use. In some aspects, immunohistochemistry techniques are complemented by the use of histological stains and/or DNA ploidy stains (e.g., as described in U.S. Pat. No. 6,165,734, the entirety of which is incorporated by reference herein. RNA samples can also be obtained (e.g., for RT-PCR assays). See, as described in Taylor et al., 1998, *J. Pathol.* 184(3): 332–335.

In situ hybridization (ISH) and Fluorescent In Situ Hybridization (FISH)

In another aspect, the biomolecule of interest being profiled is a nucleic acid and is detected using an in situ hybridization technique such as ISH or FISH. In these techniques, generally labels are attached to nucleic acid probes that allow hybridization of the probes to their complementary sequences in a tissue/cell to be visualized under a microscope. ISH probes have chromogenic markers and their binding can be observed by traditional light microscopy. FISH probes have a fluorescent markers bonded thereto (directly or indirectly) and their binding must be visualized through the use of a fluorescent microscope. Sections prepared from frozen donor samples can be hybridized with nucleic acid probes using methods routine in the art, described in, for example, Ausubel et al., 1992, *Short Protocols in Molecular Biology*, (John Wiley and Sons, Inc.), pp. 14–15 to 14–16, the entirety of which is incorporated by reference herein. ISH or FISH can be performed with one or more amplification steps, i.e., such as by performing in situ PCR or in situ RT-PCR. A detailed description of these techniques is presented in Ausubel, et al., 1992, supra, pp. 14–37 to 14–49 and in Nuovo, 1996, *Scanning Microsc. Suppl.* 10: 49–55.

In addition to detecting specific nucleic acids (e.g., genes or transcripts), ISH or FISH probes or other nucleic acid molecular probes (e.g., DAPI, acridine orange, and the like) can also be used to evaluate the absolute amounts of nucleic acids in cells within a tissue/cell sample (e.g., to determine the copy number of nucleic acids on the tissue) since changes in copy number of nucleic acids are often associated with the development of pathology. In this aspect, preferably both control and test tissue samples are provided on a single substrate (e.g., as part of a single microarray or by using a profile array substrate) in order to enable a user to perform a side-by-side comparison of signal obtained under substantially identical conditions. Preferably, an optical system in communication with the microarray is used to quantitate and compare the amount of signal obtained (e.g., determining a ratio of signal of from a test sample and control sample). In one aspect, the optical system comprises a light source in communication with the microarray for transmitting light to one or more samples on the array (e.g., such as in a CCD device), and a light receiving element for receiving light transmitted by one or more samples on the array. Preferably, the light receiving element transmits this light to a detector which converts light into an electrical signal which is proportional to the amount of light received. The detector, in turn, is in communication with a processor for storing and or displaying the electrical signal. In one aspect, an image is displayed of one or more samples on the array.

Molecular profiling can be complemented by techniques which evaluate the characteristics of nucleic acids in tissue/cell samples on the microarray. For example, microarrays can be assayed for the presence of cell death in one or more sample in the microarrays by detecting the presence of DNA fragmentation (e.g., such as generated by apoptosis) in samples on the microarrays, such as by performing TUNEL assays (see, e.g., as described in U.S. Pat. No. 6,160,106 and U.S. Pat. No. 6,140,484, the entireties of which are incorporated by reference herein). In TUNEL, the free 3'-OH termini generated by DNA fragmentation can be labeled using modified nucleotides (e.g., biotin-dUTP, DIG-dUTP, fluorescein-dUTP and the like) in the presence of terminal deoxynucleotidyl transferase (TdT). The incorporation of modified nucleotides can be detected using an antibody which specifically recognizes the modification and which itself is coupled to a detectable molecule such as a reporter enzyme (e.g., alkaline phosphatase)

Microarrays can also be evaluated to detect the presence or absence of methylation in one or more cells in samples on the array. In situ methods of identifying methylated sequences are described in U.S. Pat. No. 6,017,704, for example, the entirety of which is incorporated by reference herein. The method comprises contacting a nucleic acid-containing specimen with an agent that modifies unmethylated cytosine, amplifying the CpG-containing nucleic acid in the specimen by means of CpG-specific oligonucleotide primers which distinguish the distinguish between modified methylated and non-methylated nucleic acids, and detecting the methylated nucleic acids by detecting amplification products. The method relies on using the PCR reaction itself to distinguish between modified (e.g., chemically modified) methylated and unmethylated DNA.

In a preferred aspect of the invention, data relating to the reactivity of different sublocations in the microarray with one or more molecular probes are entered into a database, and information relating to biomolecule(s) being evaluated by the probe(s) is made accessible, along with other data relating to the samples at each sublocation on the array, to the user. Molecular profiling data can be used to further characterize a biomolecule whose function is at least partly known; however, molecular profiling data can also be used to identify the biological role of an uncharacterized gene, e.g., by identifying aberrant physiological processes in which the expression of the gene is altered (i.e., overexpressed or underexpressed or expressed in a different form) or eliminated.

In one aspect of the invention, information relating to the individual from whom the test tissue was obtained is entered into the database. Such information can include, age, sex, weight, race, patient medical history (e.g., drug treatment history, concurrent and underlying illnesses), family medical history, and the like. Preferably, the database comprises information relating to a population of individuals for whom like information also has been obtained. Still more preferably, the database is part of a tissue information system which further comprises an information management system. The information management system comprises search functions and relationship determining functions for organizing and retrieving information in the database in response to user queries. Tissue information systems are described further in U.S. patent application Ser. No. 09/781,016, filed Feb. 9, 2001, the entirety of which is incorporated by reference herein.

In one aspect, the tissue information system is used to identify a relationship between the expression of a biological characteristic (e.g., the expression of an antigen, transcript, or genotype) and the occurrence, progression, or recurrence of a disease. In another aspect, the tissue information system identifies treatment options suited to a pattern of expression of biomolecules associated with a disease (for example, the detection of expression of estrogen receptors on samples of cancerous breast tissue would trigger the tissue information system to indicate that hormone treatment would be a suitable treatment option).

Simultaneous Assays

Microarrays comprising frozen samples are better suited than microarrays comprising paraffin-embedded samples for simultaneously evaluating proteins and nucleic acids. Thus, in one aspect, in situ hybridization and immunohistochemical evaluation are performed at the same time using frozen microarrays according to the invention. Such multi-labeling techniques are described in, for example, Zaidi et al., 2000, *J. Histochem. Cytochem.* 48(10): 1369–1375, and Kingsbury et al., 1996, *J. Neurosci. Methods* 69(2): 213–27, the entireties of which are incorporated by reference herein. In another aspect, evaluation of proteins and nucleic acids is performed sequentially on a single microarray. For example, cell samples can be obtained from the microarray itself after performing histological evaluations and used for PCR and/or RT-PCR assays (see, e.g., as described in Fernandez et al., 1997, *Mol. Carcinog.* 20(3): 317–326.

Cancer Diagnosis and/or Prognosis

In one aspect, microarrays according to the invention are used to assay the expression and/or form of a cancer-specific marker or tumor-specific antigen. As used herein, "a cancer-specific marker" or a "tumor-specific antigen" is a biomolecule which is expressed preferentially on cancer cells and tumor cells, respectively, and is not expressed or is expressed to small degree in non-cancer/tumor cells of an adult individual. A cancer-specific marker is any biomolecule that is involved in or correlates with the pathogenesis of a cancer, and can act in a positive or negative manner, as long some aspect of its expression or form influences or correlates with the presence or progression of cancer. While in one aspect, expressed levels of a biomolecule provide an indication of cancer progression or recurrence, in another aspect of the invention, the expressed form of a biomolecule provides the indication (e.g., a cleaved or uncleaved state, a phosphorylated or unphosphorylated state).

In one aspect, the expression characteristics of cancer-specific markers are determined in test tissue samples and compared to the expression characteristics of the marker in tissue microarrays 13 comprising both cancerous and normal tissues (either on the same or different substrates 43). Test tissue samples can be provided on different substrates or on the same substrate as the microarray (e.g., using a profile array substrate). The cancer-specific marker can be the product of a characterized gene, e.g., such as a cell growth-related polypeptide which promotes cell proliferation, or can be uncharacterized or only partially characterized (e.g., identified through the use of molecular profiling methods described above).

Non-limiting examples of cancer-specific markers include growth factors, growth factor receptors, signal transduction pathway participants, and transcription factors involved in activating genes necessary for cell proliferation. Alternatively, or in addition, cell proliferative genes can function to suppress cell proliferation. Non-limiting examples include tumor suppressor genes (e.g., p57kip2, p53, Rb) and growth factors that act in a negative manner (e.g., TGF-β). A loss or alteration in the function of a negatively acting growth regulator often has a positive effect on cell proliferation.

The so-called tumor antigens are also included among the growth-related polypeptides. Tumor antigens are a class of protein markers that tend to be expressed to a greater extent by transformed tumor cells than by non-transformed cells. As such, tumor antigens can be expressed by non-tumor cells, although usually at lower concentrations or during an earlier developmental stage of a tissue or organism. Tumor antigens include, but are not limited to, prostate specific antigen (PSA; Osterling, 1991, J. Urol. 145: 907–923), epithelial membrane antigen (multiple epithelial carcinomas; Pinkus et al., 1986, *Am. J. Clin. Pathol.* 85: 269–277), CYFRA 21-1 (lung cancer; Lai et al., 1999, *Jpn. J. Clin. Oncol.* 29: 421–421) and Ep-CAM (pan-carcinoma; Chaubal et al., 1999, *Anticancer Res.* 19: 2237–2242). Additional examples of tumor antigens include CA125 (ovarian cancer), intact monoclonal immunoglobulin or light chain fragments (myeloma), and the beta subunit of human chorionic gonadotropin (HCG, germ cell tumors).

A sub-category of tumor antigens includes the oncofetal tumor antigens. The oncofetal tumor antigens alphafetoprotein and carcinoembryonic antigen (CEA) are usually only highly expressed in developing embryos, but are frequently highly expressed by tumors of the liver and colon, respectively, in adults. Other oncofetal tumor antigens include, but are not limited to, placental alkaline phosphatase (Deonarain et al., 1997, *Protein Eng.* 10: 89–98; Travers & Bodmer, 1984, *Int. J. Cancer* 33: 633–641), sialyl-Lewis X (adenocarcinoma, Wittig et al., 1996, *Int. J. Cancer* 67: 80–85), CA-125 and CA-19 (gastrointestinal, hepatic, and gynecological tumors; Pitkanen et al., 1994, *Pediatr. Res.* 35: 205–208), TAG-72 (colorectal tumors; Gaudagni et al., 1996, *Anticancer Res.* 16: 2141–2148), epithelial glycoprotein 2 (pan-carcinoma expression; Roovers et al., 1998, *Br. J. Cancer.* 78: 1407–1416), pancreatic oncofetal antigen (Kithier et al., 1992, *Tumor Biol.* 13: 343–351), 5T4 (gastric carcinoma; Starzynska et al., 1998, *Eur. J. Gasiroenterol. Hepatol.* 10: 479–484,; alphafetoprotein receptor (multiple tumor types, particularly mammary tumors; Moro et al., 1993, *Tumour Biol.* 14: 11–130), and M2A (germ cell neoplasia; Marks et al., 1999, *Brit. J. Cancer* 80: 569–578).

The expression characteristics of cell growth-related polypeptides are critical not only to their function, but also to their usefulness as prognostic or diagnostic indicators of disease. For example, when a given polypeptide (e.g., a tumor-suppressor gene product) or the RNA encoding it is used as a diagnostic or prognostic indicator, there are several characteristics of its expression that can be relevant. First, the total level of expression in the tumor, relative to the expression in normal cells of the corresponding cell type is important. In one aspect of the invention, the total level of expression is determined by quantitating relative signals observable using molecular probes reacted with test and control samples on a microarray. For a tumor suppressor gene, for example, a lower level of the tumor suppressor gene product in tumor samples would suggest that the lack of the tumor suppressor protein can be involved in the progression of the tumor. Such correlations can be verified because the frozen microarrays according to the invention provide the opportunity to evaluate hundreds and even thousands of samples.

Even when no definitive mechanism of action in tumor etiology is known, the correlation of any expression characteristic (e.g., higher or lower expression) of a given polypeptide or RNA encoding the polypeptide with a particular clinical diagnosis or outcome in other patients makes the expression characteristics of that polypeptide or its RNA useful in the diagnosis or prognosis of disease. The level of expression of the given polypeptide or its RNA in a particular patient is used, along with the known correlation with its expression in that disease, to diagnose or predict a clinical outcome for that patient.

Other diagnostic/prognostic indications which can be identified and validated using microarrays according to the invention include the percentage of cells expressing a biomolecule in a given tissue sample, or the localization of the biomolecule within cells in a sample. For example, if a polypeptide that is normally predominantly cytoplasmic becomes predominantly nuclear in a disease, that change can be useful as a diagnostic or prognostic indicator. Still another expression characteristic that can be evaluated is a change in the conformation of a polypeptide. Conformational changes generally result from mutations to the gene encoding the polypeptide, but can also occur due to changes in the expression of a co-factor that influences the conformation of the polypeptide. Additionally, changes in post-translational modifications (e.g., phosphorylation, glycosylation, myristoylation, etc.) of a polypeptide can also be useful expression characteristics in diagnosis and/or prognosis of disease. Antibodies that distinguish between two conformations or between different modified forms of a polypeptide are known in the art (e.g., there are antibodies known in the art that distinguish the conformation of mutant from wild-type p53) and methods of making these are described further above.

In further aspects of the invention, cancer progression can be detected and/or monitored by examining the expression of the activity of a cancer-specific marker. For example, in one aspect, the activity of telomerase is monitored in situ in samples on a microarray. Methods of in situ detection of telomerase activity are known in the art and are described, for example, in U.S. Pat. No. 6,194,206, the entirety of which is incorporated by reference herein.

In some aspects, sets or panels of cancer-specific markers are used to determine the progression of cancer in a test sample. Perhaps one of the better examples of this application is the diagnosis of small round blue cell tumors in childhood. These tumors show no distinguishing morphological features but require positive identification because of their requirements for specific therapies and clinical outcomes. Immunohistochemistry (IHC) has proven to be one of the most powerful diagnostic tools to help categorize these tumors. In the majority of cases, a carefully selected panel of antibodies (e.g., directed against antigens such as neuron-specific enolase (NSE), Mic-2 gene product, leukocyte-common antigen (LCA), vimentin, chromogranin, cytokeratin (CK), epithelial membrane antigen (EMA)) can assist in identifying most of the small blue round tumors such as leukemia/lymphoma, Ewing's Sarcoma, rhabdomyosarcoma, and mesenchymal chrondrosarcoma (see, e.g., Brahmi et al., 2001, *Diagn Cytopathol.* 24(4): 233–239, the entirety of which is incorporated by reference herein).

Although no one specific antibody is diagnostic, each tumor will have a specific pattern of staining using such a panel of antibodies. Therefore, in one aspect of the invention, a plurality of substantially identical microarrays are evaluated, preferably in parallel, using panels of antibodies directed against, for example, NSE, Mic-2 gene product, LCA, vimentin, chromogranin, CK, EMA, and the like, to provide a diagnosis to a patient suspected of having such a tumor.

Validating Diagnostic Biomolecules Identified In Other Arrays

In a preferred aspect of the invention, frozen tissue microarrays are used to validate results obtained through the analysis of other types of microarrays. For example, in one aspect, a nucleic acid array comprising expressed sequences is hybridized to a sample of labeled nucleic acids from a test tissue sample (e.g., a sample from a patient with an aberrant physiological process such as a disease) to identify one or more oligonucleotide probes on the array that hybridize to nucleic acids in the sample and/or to identify nucleic acids which fail to hybridize. Aberrantly expressed nucleic acids (e.g., nucleic acids expressed in the test sample but not in a control sample from a normal patient or from a non-diseased tissue or cell, or nucleic acids not expressed in the test sample which are expressed in the control sample) are identified and their sequence determined based on the address of the nucleic acid which hybridized or failed to hybridize in the array. Nucleic acids probes ("test diagnostic probes") comprising the same or substantially the same sequence (e.g., having sufficient sequence identity to identify the same targets in a hybridization assay) are subsequently reacted with frozen microarrays according to the invention to identify the expression pattern of the test diagnostic probes in one or more donor samples from demographically matched test patients sharing the same aberrant physiological process and in demographically matched control patients (the test and control patients sharing demographic characteristics with each other except for the presence of the aberrant physiological process in the test patients). Preferably, the expression of test diagnostic probes is evaluated in whole body arrays from a plurality of patients. Still more preferably, the microarray comprises cells from a bodily fluid to determine if the test diagnostic probe could be monitored in a readily obtainable sample. Similarly, peptide arrays or polypeptide arrays or protein arrays (e.g., comprising a plurality of different antibodies) can be used to identify aberrantly expressed peptides/polypeptides and this expression can be verified in frozen tissue microarrays using suitable reactive antibodies specifically recognizing these peptides/polypeptides.

In one aspect, cell microarrays comprising a plurality of frozen cancer cells (e.g., from different cancer cell lines) are used to identify target diagnostic probes diagnostic of cancer. Such probes can be validated using frozen tissue microarrays according to the invention comprising samples obtained from a plurality of patients having different types of cancer. In one aspect, the microarrays are used to identify universal cancer markers expressed in substantially all (at least about 75%, and preferably, at least about 95%) of cancer cells. In other aspects, the microarrays are used to identify type specific cancer cell markers (e.g., expressed predominantly in specific types and/or grades of cancers and not in other types and/or grades of cancers).

Selecting Promising Drug Targets

Microarrays according to the invention also can be used to identify drug targets whose interactions with one or a plurality of biomolecules is associated with disease. For example, drug targets can include binding pairs such as receptor: ligand pairs whose binding triggers an aberrant physiological response when either or both of the receptor or ligand is mutated or improperly modified. Alternatively, a drug target can be a molecule which is overexpressed or underexpressed during a pathological process. By identifying drug targets, drugs can be screened for which can restore a cell's/tissue's normal physiological functioning. For example, where a drug target is a receptor: ligand pair, a suitable drug might be an antagonist of ligand binding. Alternatively, where a drug target is a molecule which is overexpressed or underexpressed, a suitable drug could be a molecule (e.g., a therapeutic antibody, polypeptide, or nucleic acid) which restores substantially normal levels of the drug target.

Test probes are used to identify a biomolecule or set of biomolecules whose expression is diagnostic of a trait (e.g., such as by using the molecular profiling techniques described above). In one aspect, identifying diagnostic biomolecules is performed by determining which molecules on a microarray are substantially always present in a disease sample and substantially always absent in a healthy sample, or substantially always absent in a disease sample and substantially always present in a healthy sample, or substantially always present in a certain form or amount in a disease sample and substantially always present in a certain other form or amount in a healthy sample. By "substantially always" it is meant that there is a statistically significant correlation to within 95% confidence levels between the expression/form of the biomolecule or set of biomolecules and the presence of an aberrant physiological process, such as a disease.

Test probes identifying diagnostic biomolecules are then contacted with a microarray substrate to identify the presence, amount, and/or form of diagnostic biomolecules in a microarray comprising different types of healthy and/or diseased tissues. In this way, a correlation between the expression of the diagnostic biomolecule(s) and a disease state can be validated.

Preferably, expression of a diagnostic biomolecule or set of biomolecules is examined in a microarray comprising tissues from a drug-treated patient and tissues from an untreated diseased patient and/or from a healthy patient. In this aspect, the efficacy of the drug is monitored by determining whether the expression profile of the diagnostic molecule(s) returns to a profile which is substantially similar (e.g., not significantly different as determined by routine statistical testing) to the expression profile of the same biomolecule(s) in a healthy patient or a patient who has achieved a desired therapeutic outcome. A drug is identified as useful for further testing when the expression pattern in the test tissue is substantially the same as the expression pattern within the healthy tissue (to within 95% confidence levels) or is within about 10% of the levels of the biomolecule observed in a normal patient or a patient who has achieved a desired therapeutic outcome.

Batch Control of Molecular Probes

The frozen microarrays according to the invention provide multiple control samples for simultaneous staining to provide an assessment of the sensitivity and specificity of a molecular probe, such as an antibody. Instead of reacting one tissue/cell as a known positive control, the substrates provide the option of reacting, for example, about 25 controls or more, all on the same slide. In one aspect, the control tissue/cell samples are already known to be positive or negative for the expression of antigens recognized by the most common clinical antibodies used. Suitable commercially sold antibodies can be found through many internet access sites, such as http://www.antibodyresource.com/findantibody.html. Pre-stained microarrays can be provided in kits along with unstained substantially identical microarrays, and/or with one or more molecular probes as controls for additional evaluations.

In one aspect of the invention, frozen microarrays are provided comprising a plurality of tissues from different tumor types. For example, in one aspect, a breast cancer microarray can be provided which comprises at least 20 samples of different breast cancers (i.e., from genetically unrelated individuals) and 1–5 samples of normal breast tissue arrayed at different sublocations on the microarray. The microarray can be evaluated using a molecular probe or panel of molecular probes to confirm that the microarray has different known reactivities with a molecular probe, such as staining qualities (e.g., amount of staining and/or location of staining) among different samples on the array. For example, in one aspect, two common breast cancer marker antibodies, such as an anti-Estrogen receptor antibody and an anti-c-erbB-2 antibody are used to stain the sublocations in the microarray. By comparing the staining quality, location and intensity of antibody staining of samples comprising known amounts of estrogen receptor and c-erbB-2 antigens, the staining of a test sample comprising breast tissue from a patient suspected of having cancer can be evaluated with a higher degree of certainty.

Routine Histology Lab Quality Control: Automated or Manual Methods

Frozen microarrays according to the invention can also be used in daily quality control for immunohistochemistry, or in other histological procedures that rely on molecular probes (e.g., nucleic acid hybridizations, and the like). A normal frozen microarray comprising a plurality of different non-diseased donor samples is ideally suited for this purpose. By comparing substrate slides stained daily with previous daily runs that have been judged to have "optimal reactivity," deviations in specificity and sensitivity in a molecular probe can be observed and corrections made. In one aspect of the invention, comparing is done visually. However, in another aspect, comparing is done by collecting optical data (e.g., spectral data) from labeled molecular probes using an optical system in communication with the microarray as described above to obtain quantitative measurements of probe reactivity with samples on the microarray. In one aspect, the quantitative measurements so obtained are compared to measurements identified as optimal, and a molecular probe is identified as one to use in further tests when its optical measurements are substantially similar to those of the optimal measurement (as determined by routine statistical analysis with confidence levels set at 95%). In another aspect of the invention, the batch testing and identification of the molecular probe is automated. It should be obvious to those of ordinary skill in the art that batch testing can be done of any reactive molecular probe (e.g., antibody probes, a nucleic acid probe, aptamer probe, enzyme probe, and the like).

Screening Of New Commercial Antibodies: Automated Or Manual Methods

All newly acquired lots of commercial antibodies should be tested prior to diagnostic use for optimal titration and staining specificity. This can easily be accomplished with the use of the appropriate microarrays suitable for the specific antibody being tested. For example, in one aspect, a new batch of PSA antibody is evaluated on at least 5–100 individual prostate tumors by using a microarray comprising a plurality of prostate tumor samples. Preferably, an array is used which comprises at least one sample known to express an antigen the antibody recognizes and at least one sample known not to express an antigen the antibody recognizes.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

We claim:

1. A method for preparing a microarray of frozen tissue and/or cell samples comprising the steps of:
   (a) obtaining a donor sample from a donor block comprising a tissue or cell sample embedded in frozen embedding material;
   (b) providing a recipient block comprising a frozen embedding material;
   (c) providing a tissue microarrayer comprising a cooling chamber for receiving the recipient block and maintaining the recipient block in a frozen condition; said cooling chamber moveable in an x- and y- direction relative to a fixed horizontal surface;
   (d) generating a hole in said recipient block sized to receive said donor sample;
   (e) filling said hole in said recipient block with said donor sample;
   (f) repeating steps (a)–(e) to create a microarray block comprising a plurality of donor tissue and/or cell samples embedded in a block of frozen embedding material, each of said donor samples having a known location in said block;
   (g) sectioning said microarray block to generate a section comprising portions of said plurality of donor samples, each portion of each donor sample at a different sublocation in the section at coordinates corresponding to coordinates of the donor sample in the microarray block from which each portion was obtained; and
   (h) placing said section on a substrate such that said portions at different sublocations are stably associated with said substrate, thereby generating said microarray.

2. The method according to claim 1, wherein said microarray block comprises about 10 to about 1200 samples.

3. The method according to claim 1, wherein at least one of said donor samples is a tissue sample.

4. The method according to claim 1, wherein at least one of said donor samples is a cell sample.

5. The method according to claim 1, wherein said obtaining is performed by using a coring needle comprising a cutting edge and wall defining a lumen to core a donor sample.

6. The method according to claim 5, wherein said core is in the shape of a cylinder.

7. The method according to claim 6, wherein said core is about 0.3 mm in diameter.

8. The method according to claim 6, wherein said core is about 0.6 mm in diameter.

9. The method according to claim 6, wherein said core is greater than about 0.6 mm.

10. A method of generating a microarray block, comprising the steps of:
    (a) obtaining a donor sample from a donor block comprising a tissue or cell sample embedded in frozen embedding material;
    (b) providing a recipient block comprising a frozen embedding material,
    (c) providing a tissue microarrayer comprising a cooling chamber for receiving the recipient block and maintaining the recipient block in a frozen condition; said cooling chamber moveable in an x- and y- direction relative to a fixed horizontal surface;
    (d) generating a hole in said recipient block with the at least one coring needle wherein the hole is sized to receive said frozen donor sample; and
    (e) filling said hole with said donor sample.

11. The method according to claim 10, further comprising repeating steps (a) to (e) multiple times.

12. The method according to claim 1 or 11, wherein said method is automated.

13. The method according to claim 12, wherein information relating to the location of each donor sample in said recipient block is stored in a database.

* * * * *